United States Patent [19]

Nakagawa et al.

[11] Patent Number: 4,774,053

[45] Date of Patent: Sep. 27, 1988

[54] SILVER HALIDE PHOTOGRAPHIC LIGHT-SENSITIVE MATERIAL

[75] Inventors: Satoshi Nakagawa; Shuji Kida; Yasuhiko Kawashima; Kosaku Masuda, all of Hino, Japan

[73] Assignee: Konishiroku Photo Industry Co., Ltd., Tokyo, Japan

[21] Appl. No.: 120,702

[22] Filed: Nov. 13, 1987

Related U.S. Application Data

[63] Continuation of Ser. No. 45,783, Apr. 29, 1987, abandoned, which is a continuation of Ser. No. 816,678, Jan. 3, 1986, abandoned, which is a continuation of Ser. No. 552,086, Nov. 15, 1983, abandoned.

[30] Foreign Application Priority Data

Nov. 16, 1982 [JP] Japan ................................. 57-201592

[51] Int. Cl.$^4$ ........................... G03C 7/18; G03C 7/20
[52] U.S. Cl. ................................. 430/504; 430/505; 430/506
[58] Field of Search ....................... 430/504–506, 430/509

[56] References Cited

U.S. PATENT DOCUMENTS 3,227,550  1/1966  Whitmore et al. .................. 430/555
4,184,876  1/1980  Eeles et al. ....................... 430/505
4,414,308  11/1983 Hamada et al. .................... 430/506
4,420,556  12/1983 Booms et al. ...................... 430/557

FOREIGN PATENT DOCUMENTS 0096873  12/1983  European Pat. Off. .

*Primary Examiner*—Richard L. Schilling
*Attorney, Agent, or Firm*—Jordan B. Bierman

[57] ABSTRACT

Silver halide photographic light-sensitive material comprising a support having a plurality of silver halide emulsion layers which are sensitive to the same spectral region and having different speeds and at least one light-sensitive layer comprising a nondiffusible coupler, which upon reaction with an oxidized product of a color developing agent is capable of forming a nondiffusible dye, wherein the silver halide emulsion layer having the greatest speed of said plurality of silver halide emulsion layers sensitive to a particular spectral region contains a nondiffusible coupler which, upon reaction with an oxidized product of a color developing agent, is capable of producing a moveable dye, and a silver halide emulsion having a speed slower than said fastest speed layer contains a nondiffusible compound which, upon reaction with an oxidized product of a color developing agent, is capable of releasing a development inhibitor material.

28 Claims, No Drawings

SILVER HALIDE PHOTOGRAPHIC LIGHT-SENSITIVE MATERIAL

This application is a continuation of application Ser. No. 045,785, filed Apr. 29, 1987, now abandoned, which is a continuation of application Ser. No. 816,678, filed Jan 3, 1986, now abandoned which is a continuation of application Ser. No. 552,086, filed 11/15/83, now abandoned.

BACKGROUND OF INVENTION

The present invention relates to a silver halide photographic light-sensitive material, and more particularly to a silver halide photographic light-sensitive material having improved graininess and excellent sharpness.

In recent years, there has been remarkable technological progress for increasing the speed of as well as for improving the image quality of silver halide photographic light-sensitive materials, particularly silver halide color photographic light-sensitive materials. That is, to meet the need for increasing the speed, improvements have been made by providing two or more emulsion layers differing in the speed but having sensitivity to the same spectral region and by the use of two-equivalent-type couplers, while for improving the image quality, the development and use of DIR compounds have played an important role.

Particularly, the above-mentioned DIR compound for use in the improvement on the image quality, i.e., the graininess and sharpness, by its coupling reaction with the oxidized product of a color developing agent, releases imagewise a development inhibitor to thereby inhibit the silver development to prevent possible enormous growth of dye cloud, and concurrently carries out gradation control, thus resulting in the increase in color forming points to improve the graininess. At the same time, the imagewise produced development inhibitor diffuses to thereby further strengthen the edge effect, thus also improving the sharpness.

However, color photographic light-sensitive materials for amateur use in recent years show a marked tendency to become increasingly smaller in the film format for ease of handling, simplification of the processing, or for the purpose of silver saving. This tendency naturally leads to the need for a larger magnification of a negative film to make enlarged photographic prints, so that a further improvement of the graininess, particularly of the graininess in a low exposure scale is desired.

In ordinary silver halide color photographic light-sensitive materials, in general the lower the exposure scale, the less do the color forming points become, so that the graininess becomes worse. In the present situation where the provision of a plurality of emulsion layers sensitive to the same spectral region but differing in the speed is most popularized, even if an attempt is made to increase color forming points by minimizing the silver halide particle size of a high-speed emulsion layer, there would be naturally a limit to the attempt in respect of the speed.

In contrast to this, a method for improving the graininess by use of a nondiffusible coupler capable of producing a movable dye is recently disclosed in Japanese Patent Publication Open to Public Inspection (hereinafter referred to as Japanese Patent O.P.I. Publication) No. 82837/1982. The technique in this method, as described in the publication, shows an improving effect upon the graininess but does not come up to the improvement on the sharpness. The above technique is therefore desirable to be utilized in a layer for producing an yellow dye, to which color the naked eye is less sensitive, so that the technique lacks the actual improvement effect on the graininess of a photographic image that is easily distinguishable by the naked eye.

It is therefore an object of the present invention to provide a silver halide photographic light-sensitive material which is capable of making up for the above disadvantages, and of forming a photographic image excellent not only in the graininess but also in the sharpness.

DESCRIPTION OF INVENTION

As a result of our continued various investigations, it has now been found that the above object can be accomplished by the following silver halide photographic light-sensitive material comprising a support having thereon plural silver halide emulsion layers which are respectively different in speed but have the sensitivity thereof in the same spectral region and at least one light-sensitive layer containing a nondiffusible coupler capable of forming a nondiffusible dye by the reaction thereof with the oxidized product of a color developing agent, wherein the silver halide emulsion layer having highest speed among said plural silver halide emulsion layers contains a nondiffusible coupler which reacts with the oxidized product of a color developing agent to thereby produce a movable dye, and a silver halide emulsion layer having a lower speed than that of said silver halide emulsion layer among said plural silver halide emulsion layers having highest speed contains a nondiffusible compound which reacts with the oxidized product of the color developing agent to thereby release a development inhibitor material.

Namely, the present invention is characterized by such a silver halide photographic light-sensitive material as comprising not less than two emulsion layers differing in the speed but having the sensitivity thereof to the same spectral region and containing a nondiffusible dye-formable nondiffusible coupler, the silver halide emulsion layers containing in the highest speed-having emulsion layer thereof a movable dye-producible nondiffusible coupler, and in another emulsion layer thereof having lower speed than that of the highest-speed emulsion layer a compound capable of releasing a development inhibitor material (hereinafter referred to as "DIR compound") concurrently with the nondiffusible dye-producible coupler.

In such the construction-having silver halide photographic light-sensitive material of the present invention, generally, when subjected to a small exposure, the large-size and high-speed silver halide particles-having emulsion layer alone senses to the exposure light, so that the graininess becomes deteriorated, while on the contrary the highest-speed emulsion of the present invention, as above-described, contains a movable dye-formable coupler, so that a movable dye cloud produced by the reaction of the coupler with the oxidized product of a color developing agent spreads into both highest-speed and lower-speed emulsion layers, thus having improving effect upon the graininess.

And when subjected further to a large exposure, not only the highest-speed emulsion layer but also a lower-speed emulsion layer sense to the exposure light, and then the DIR compound contained in the lower-speed emulsion layer commences the action thereof during a color developing process.

The DIR compound, which will be described in detail hereinafter, as is generally known, is one that performs a coupling reaction with the oxidized product of a color developing agent during a color developing process, thereby releasing a development inhibitor material.

The thus released development inhibitor material spreads at least into not only the DIR compound-containing emulsion layer but also the layers adjacent thereto, and belongs to the so-called diffusible compound. Accordingly, the action of the above-mentioned development inhibitor material, without staying in a same layer, comes up to the adjacent layers. When subjected to a large exposure as described above, the development inhibitor material released during a color development from the DIR compound contained in the lower-speed emulsion layer spreads into not only the DIR compound-containing lower-speed emulsion layer but also the highest-speed emulsion layer, thereby increasing the edge effect in accordance with the image-wise-distributed development inhibiting action and preventing possible deterioration of the sharpness due to the spreading of the dye accompanying the increase in the image density, thus improving the sharpness. Furthermore, the effect by the present invention, although the reason thereof is not evident, is a remarkably higher effect than a mere improvement on the graininess accompanyied by the increase in the color forming points by the use of the above DIR compound, which improvement was an unexpectedly satisfactory effect.

In addition, in the present invention, the above multi-layered light-sensitive material is prepared by coating on a support in order from the support side red-sensitive, green-sensitive and blue-sensitive emulsion layers, and when dividing one of these layers or all the layers each into silver halide emulsion layers differing in the speed, the layer closer to the support is made to be the lower-speed layer.

Therefore the application of the present invention to a color photographic light-sensitive material whose blue-sensitive silver halide emulsion layer comprises at least two layers differing in the speed enables to markedly improve the graininess as well as the sharpness of the yellow image, and further, the application of the invention to the other light-sensitive layers, i.e., the green-sensitive and red-sensitive layers also enables the improvement on the graininess and sharpness of the magenta and cyan images, respectively.

There are several types of the movable dye-producible nondiffusible coupler contained in the high-speed emulsion layer according to the present invention, and one of the types is a coupler capable of producing a dye which is so slightly movable as desired within the period of time during which the processing and drying of the sensitive-material are completed, and another is a coupler that produces a completely diffusible dye.

In the case of using the latter coupler, because of a completely diffusible dye, it is desirable to use a mordant. The mordant will be described hereinafter. The movable dye used herein includes a dye so slightly movable as can be stayed inside the emulsion layer wherein the dye is produced, and such a completely diffusible dye as diffusing as far as the adjacent layers from the above emulsion layer and is stayed inside the photographic elements by the mordant.

The movable dye-producible nondiffusible coupler in the present invention has in the coupling position thereof a stabilizing group for rendering the coupler immovable and nondiffusible and in the noncoupling position thereof a control group for controlling the moving degree of the produced dye. When the above coupler couples with the oxidized product of a color developing agent, the stabilizing group is split from the coupler, and the thereby produced dye becomes movable. The moving degree of the movable dye can be controlled by the control group; for example, in one most extreme case, the dye is controlled to become a slightly movable, and in the other most extreme case, it is controlled to become a comletely diffusible dye. Such the control group depends on the coupler's mother nucleus, another substituent introduced into the coupler, and the color developing agent used. Even if it is the same substituent, the control group, in the case of one certain coupler, may render the produced dye completely diffusible, and in the case of another, may render the produced dye slightly movable.

The above-described movable dye-reproducible nondiffusible coupler for the present invention has the formula:

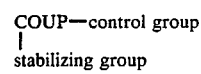

wherein COUP represents a coupler moiety for producing a dye, and the stabilizing group is a group that is linked to the above coupler moiety in the coupling position thereof and can be split from COUP during the coupling reaction between the coupler and the oxidized product of a color developing agent. And the above stabilizing group has such molecular size and form as enough for rendering the coupler nondiffusible.

The control group is a group that is linked to COUP in the noncoupling position thereof and so controls the dye produced by the coupling reaction of the coupler with the oxidized product of a color developing agent as to become slightly movable as previously described or completely diffusible.

The above COUP represents the coupler's mother nucleus and produces a dye by the reaction thereof with the oxidized product of a color developing agent, so that it may be any known or used coupler's mother nucleus to or by those skilled in the art. For example, the usable yellow dye-producible coupler includes acylanilide-type acetanilides and benzoylacetanilides; the magenta dye-producible coupler includes pyrazolones, pyrazolotriazoles, pyrazolobenzimidazoles and indazolones; and further the cyan dye-producible coupler includes phenols and naphthols. These couplers each is capable of producing the coupler portion COUP.

The aforesaid stabilizing group has sufficient molecular size and form for rendering the coupler nondiffusible. The useful stabilizing group of the kind includes groups having alkyl components and aryl components having not less than eight carbon atoms, and preferably from 8 to 32 carbon atoms. These stabilizing groups may be ones substituted by such a group as capable of changing the reactivity of the coupler, and may also have a cross-linking group for linking the stabilizing group to the coupler moiety in the coupling position thereof. Those typical cross-linking groups of the kind includes, e.g., $$-O-, -N=N-, -N\diagdown_{Z}-$$

(wherein z is a group of atoms necessary to form a 5- to 7-member heterocyclic group) and the like. Those preferred stabilizing groups include 8- to 32 carbon atoms-having alkoxy, aryloxy, alkyloxy, arylthio and nitrogen-containing heterocyclic groups.

The foregoing control group, in one extreme case, is a group having molecular size and form suitable for rendering the produced dye slightly movable and, in the other extreme case, is an alkali-soluble group capable of rendering the dye completely diffusible.

Those preferred as the above group suitable for rendering the dye slightly movable are alkyl groups having from 1 to 1 carbon atoms and aryl groups having from 6 to 20 carbon atoms. These groups are allowed to be further substituted by a group capable of changing the spectral characteristic and diffusibility of the dye. These control groups are also allowed to have a cross-linking group for linking the same to the coupler moiety, the cross-linking group including, e.g., —O—, —S—, —CO—, —COO—, —NR—, —CONR—, —NRCO—, —SO$_2$NR—, —NRSO$_2$—, —NRCONR—(wherein R is a hydrogen atom, and alkyl group or an aryl group), and the like.

The alkali-soluble group rendering the dye completely diffusible, on the other hand, is a group capable of being ionized under a processing condition, and is a group containing, e.g., a hydroxy group, a carboxylic acid group, a sulfonic acid group, or an aminosulfonyl group, and not less than one salt thereof. These groups also are allowed to be ones having a cross-linking group for linking the group to the coupler's mother nucleus, the cross-linking group being typified by, e g., —O—, —S—, —CO—, —COO—, —NR—, —CONR—, —NRCO—, —SO$_2$NR—, —NRSO$_2$—, —NRCONR— (wherein R is a hydrogen atom, an alkyl group or aryl group), and the like.

The movable dye-producible nondiffusible coupler used in the present invention may be either one that produces a slightly movable dye or one that produces a completely diffusible dye, or both may be used together. In the case of using the completely diffusible dye-producible nondiffusible coupler, a mordant layer to be paired with the coupler is used, which mordant layer may be provided immediately on an emulsion containing this coupler or may also be disposed through such an interlayer as an inert gelatin layer, or allowed to be the topmost layer through some further emulsion layers. As another method, the above mordant may be incorporated together with the coupler into the same layer.

Among the movable dye-producible nondiffusible couplers in the present invention, those preferred yellow couplers have the formula:

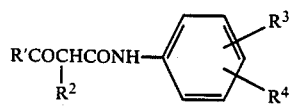  Formula (II)

wherein R$^1$ is an aryl group (such as phenyl group) or an alkyl group (such a tertiary alkyl group as t-butyl group); R$^2$ is the foregoing stabilizing group; R$^3$ is the foregoing control group; and R$^4$ represents a hydrogen atom, a halogen atom, an alkyl group or an alkoxy group and a control group.

Those preferred cyan couplers have either one of the formulas:

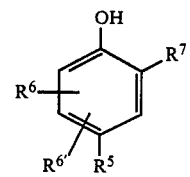  Formula (III)

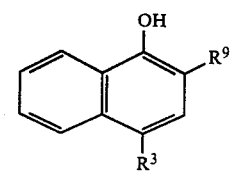  Formula (IV)

wherein R$^5$ represents a group the same as defined in the R$^2$ of Formula (II); any one of R$^6$, R$_6'$ or R$^7$ represents the foregoing control group and the other two of them are allowed to be either the same of different from each other, representing a hydrogen atom, a halogen atom, an alkyl group, an alkoxy group, an alkylamino group, or an acylamido group; and R$^8$ is a group the same as defined in R$^5$; and R$^9$ represents a control group.

Those preferred magenta couplers have either one of the formulas:

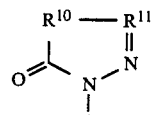  Formula (V)

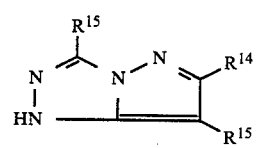  Formula (VI)

wherein R$^{10}$ represents a group the same as defined in the R$^5$ of Formula (II); R$^{11}$ represents a control group; Ar is a phenyl group which is allowed to have at least one substituent selected from the class consisting of a halogen atom, alkyl groups, alkoxy groups and amino groups, the phenyl group being allowed to have the foregoing control group; R$^{13}$ is a group as defined in R$^{10}$; and either one of and R$^{14}$ R$^{15}$ is a control group and the other is a hydrogen atom, an alkyl group, an alkoxy group, an aryl group, an amino group, or an acylamido group.

Except those particularly mentioned, the above alkyl, alkoxy, and alkylamino groups each has from 1 to 8 carbon atoms, the aryl groups each has from 6 to 10 carbon atoms, and the amino groups include primary, secondary, and tertiary amino groups. These groups and control groups are allowed to be further substituted by a halogen atom, a hydroxy group, a carboxy group, an amino group, an amido group, a carbamoyl group, a sulfamoyl group, a sulfonamido group, an alkyl group, an alkoxy group, an aryl group, or the like.

The following are typical examples of the movable dye-producible nondiffusible couplers in the present invention, but the present invention is not limited thereto.
Exemplefied Compounds:
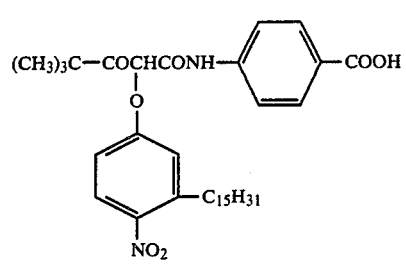
(C-1)
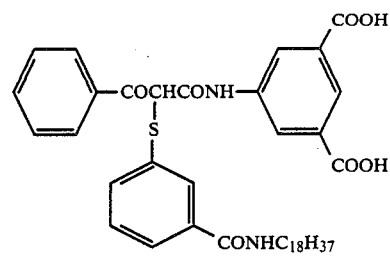
(C-2)
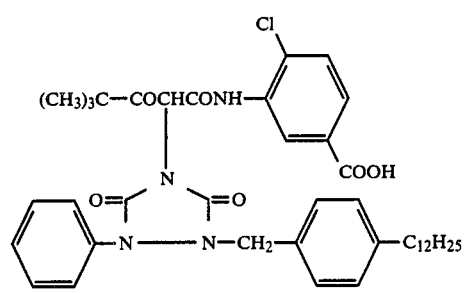
(C-3)
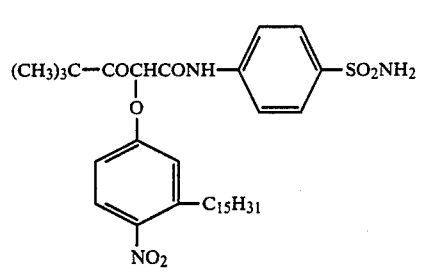
(C-4)
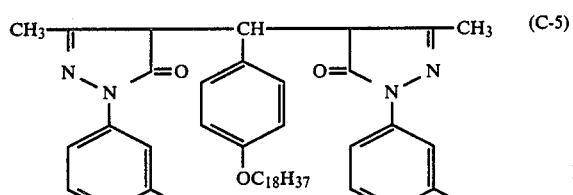
(C-5)
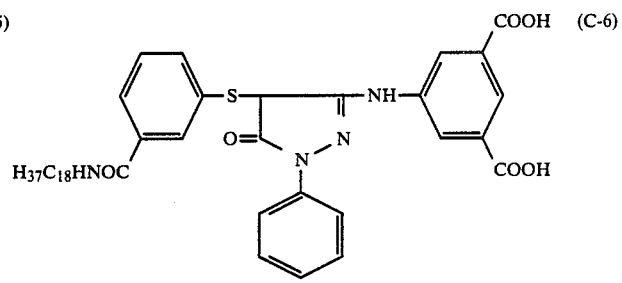
(C-6)
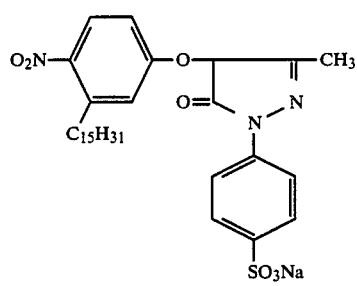
(C-7)
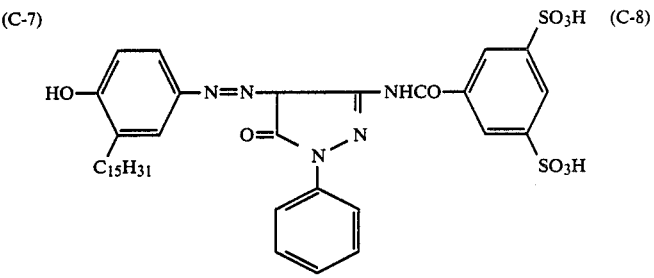
(C-8)
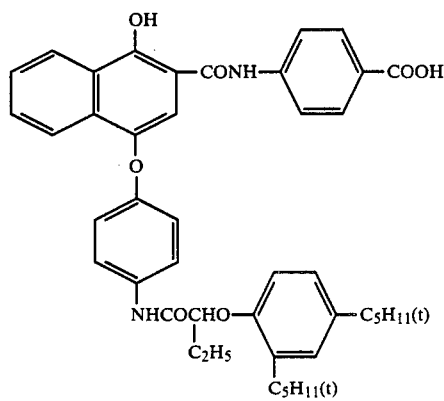
(C-9)
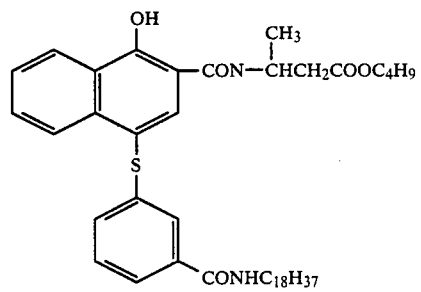
(C-10)

-continued
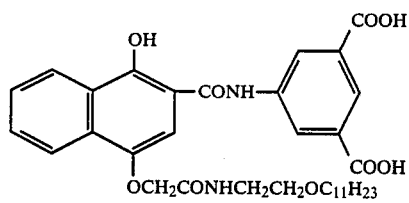
(C-11)
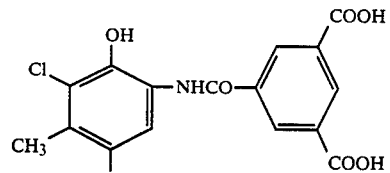
(C-12)
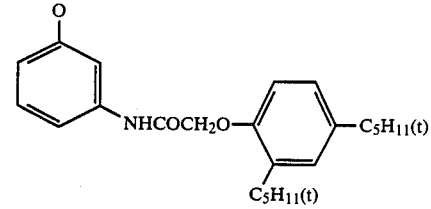
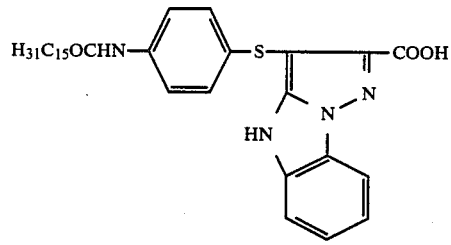
(C-13)
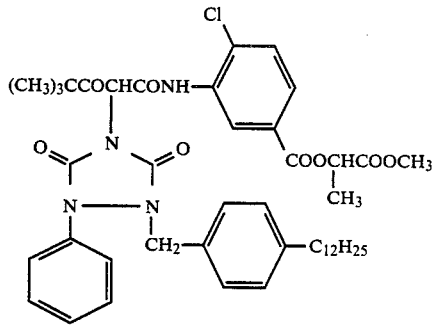
(C-14)
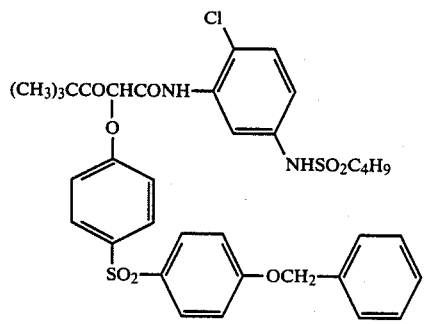
(C-15)
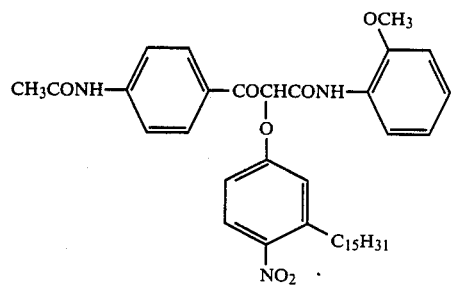
(C-16)
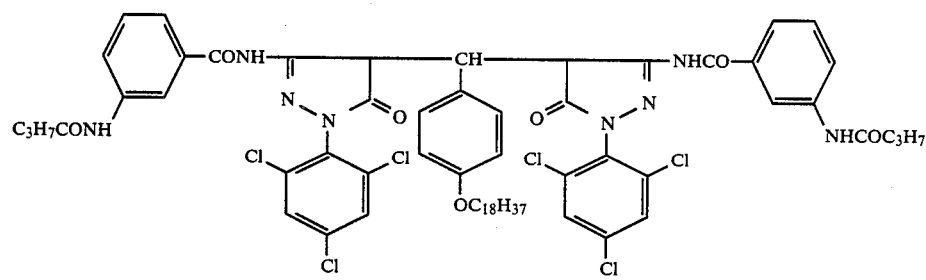
(C-17)
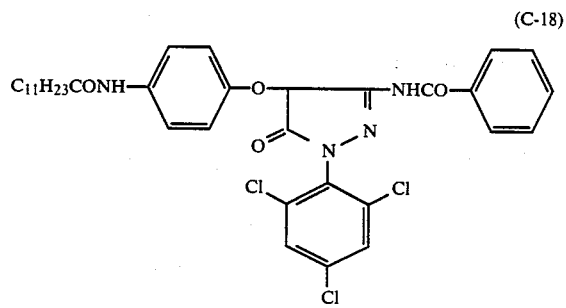
(C-18)
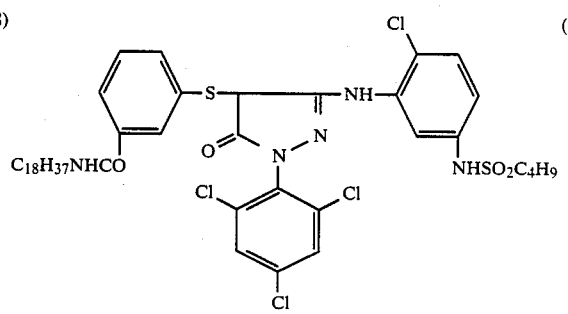
(C-19)

-continued
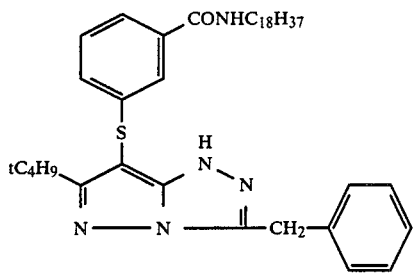 (C-20)
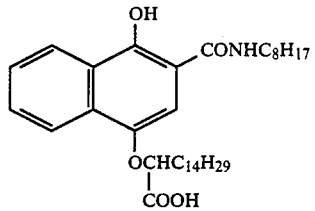 (C-21)
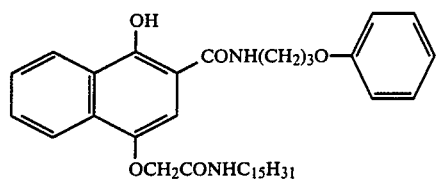 (C-22)
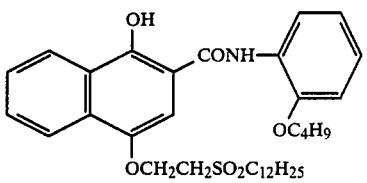 (C-23)
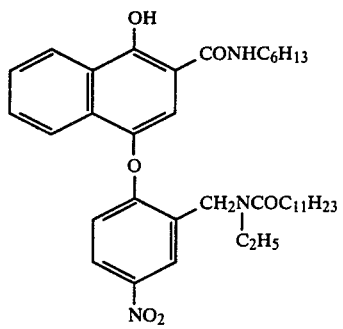 (C-24)
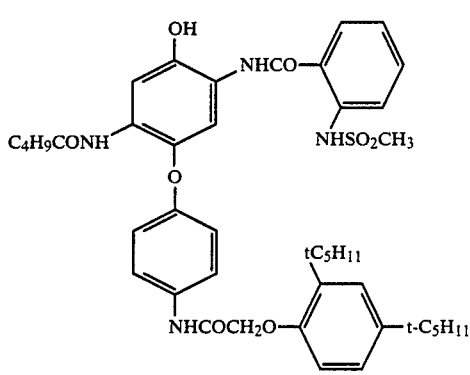 (C-25)
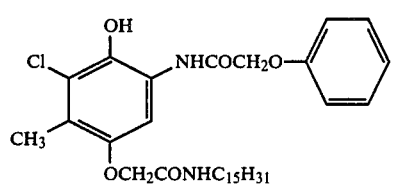 (C-26)
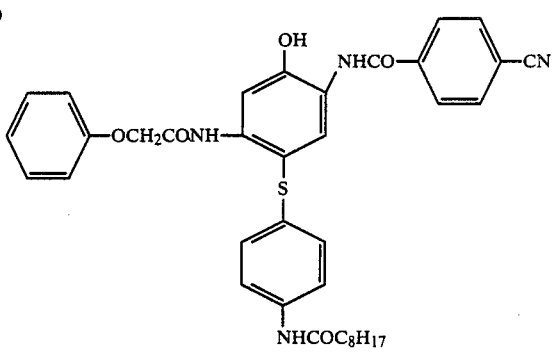 (C-27)
Typical synthesis examples of some of the above compounds will be subsequently described below. Those compounds not described in the following sysntehsis examples can also be easily synthesized in similar manners to the following examples.
SYNTHESIS EXAMPLE 1
Synthesis of Exemplified Compound C-3:
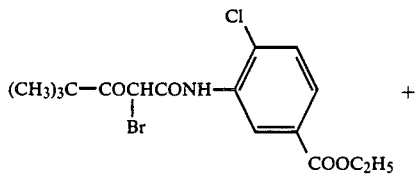
-continued
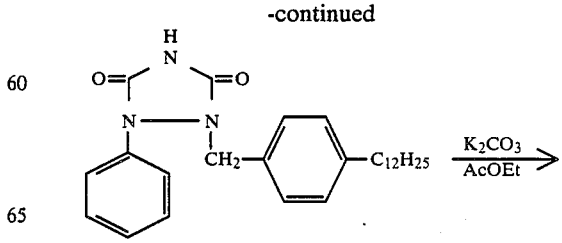

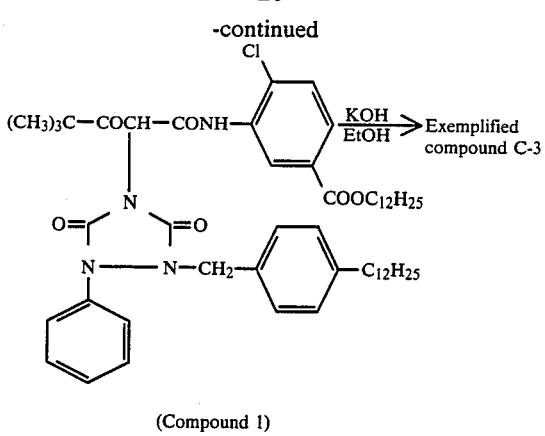

(Compound 1)

(Synthesis of Compound 1)

Into 100 ml of ethyl acetate are dissolved 7.4 g (.018 mole) of α-pivalyl-α-bromo-2-chloro-5-ethoxycarbonyl-acetanilide and 8.0 g (0.018 mole) of 3-phenyl-4-(4-dodecyl-benzyl) urazole, and to the solution are added 1.3 g (0.009 mole) of anhydrous potassium carbonate, and the mixture is refluxed by heating for three hours. To the reaction product are added 200 ml of water to extract the ethyl acetate stratum, which is then concentrated to thereby obtain an yellow viscous substance as Compound 1.

(Synthesis of Exemplified Compound C-3)

The thus obtained Compound 1 is dissolved into 50 ml of ethyl alcohol, and to the solution is added a solution of 5.0 g of potassium hydroxide dissolved into 10 ml of water to effect a reaction for two hours. The resulting reaction product is added to an iced water containing 10 ml of concentrated hydrochloric acid with stirring, whereby a white solid product is deposited, which is filtrated, washed and then dried, and after that, is recrystallized with use of ethyl acetate-hexane, whereby 10.3 g of Exemplified Compound C-3 are obtained.

SYNTHESIS EXAMPLE 2

Synthesis of Exemplified Compound C-5:

Into 200 ml of ethyl alcohol are dissolved 10.6 g (0.024 mole) of 1-(3-carboxyphenyl)-3-methyl pyrazolone and 9.1 lg (0.012 mole) of 4-octadecyloxybenzaldehyde, and to the solution are added three drops of triethylamine, and the reaction of the mixture takes place for 5 hours. After concentration, the resulting solid substance is washed with ethyl acetate to thereby obtain 14.6 g of Exemplified Compound C-5.

SYNTHESIS EXAMPLE 3

Synthesis of Exemplified Compound C-9:

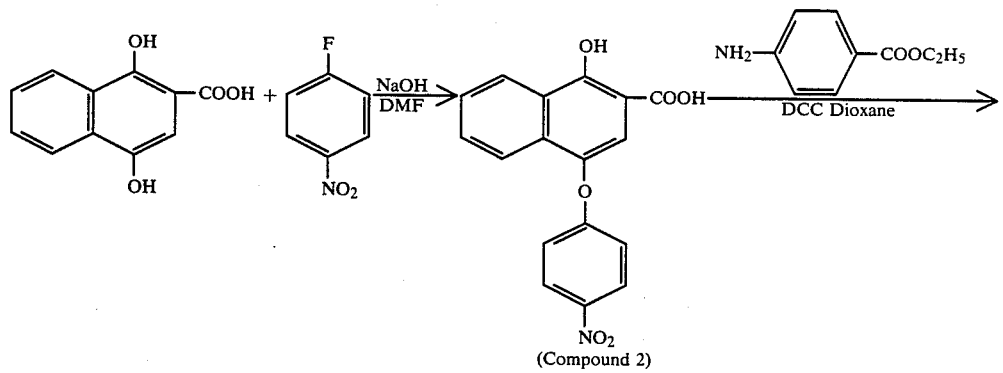

(Compound 2)

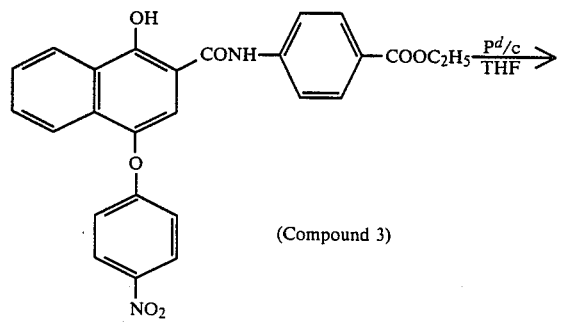

(Compound 3)

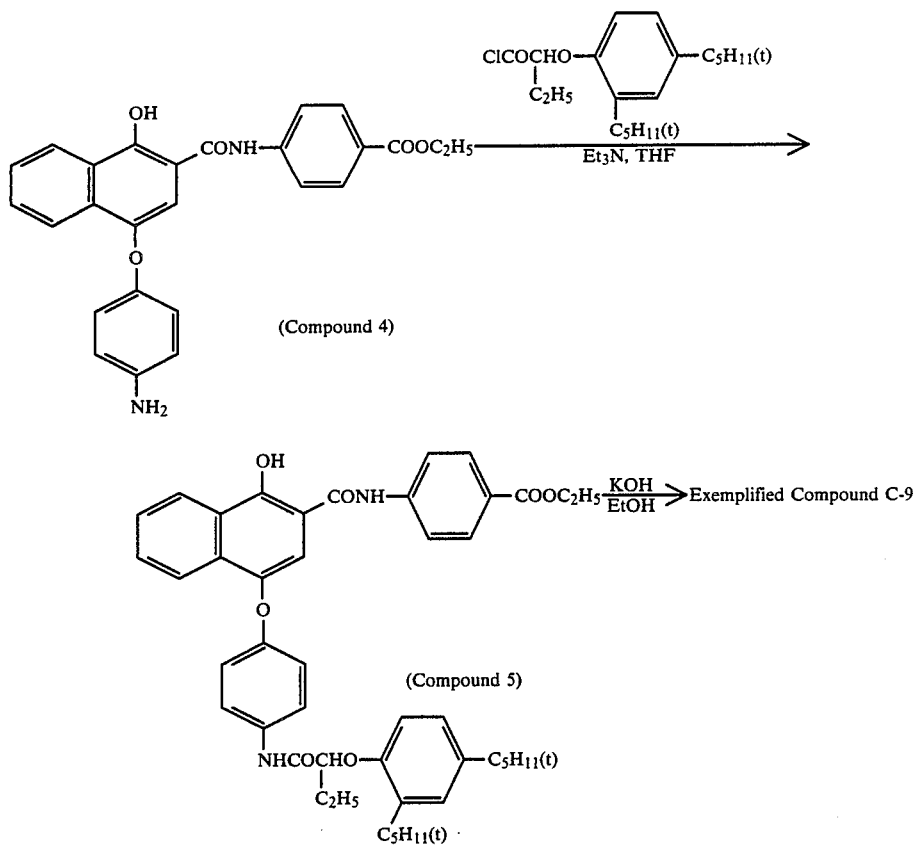

(Compound 4)

(Compound 5)

(Synthesis of Compound 2)

Twenty point four grams (0.1 mole) of 1,4-dihydroxy-2-naphthoic acid and 14.1 g (0.1 mole) of p-nitrofluorobenzene are dissolved into 300 ml of dimethylformamide, and to the solution, with conducting a nitrogen gas thereinto, is added a solution of 8.5 g (0.2 mole) of sodium hydroxide dissolved into 20 ml of water, and the reaction of the mixture takes place for an hour. The resulting reaction product is added to iced water containing 20 ml of concentrated hydrochloric acid with stirring, thereby producing a thick syrup-like solid, which is then heated over a water bath with stirring to thereby become solidified. The resulting crystals are filtrated, washed with water and then with acetonitrile, and then dried, whereby 23.2 g of a light yellow solid substance as Compound 2 were obtained.

(Synthesis of Compound 3)

Twenty-one point eight grams (0.067 mole) of the above-obtained Compound 2 and 11.1 g (0.067 mole) of ethyl p-aminobenzoate are dissolved into 200 ml of dioxane, and to the mixture were added 13.8 g (0.067 mole) of N,N'-dicyclohexylcarbodiimide, and the reaction of the mixture takes place for two hours. The deposited urea is filtered off and then washed three times with 200 ml of heated dioxane. The filtrate is concentrated, and the resulting solid substance is washed with heated ethyl acetate, whereby 21 g of an yellowish green solid as Compound 3 are obtained.

(Synthesis of Compound 4)

Twenty-one grams of the above-obtained Compound 3 are dissolved into 450 ml of tetrahydrofuran, and to the solution is made catalytic hydrogenation with use of 4 g of a 5% palladium carbon catalyst over a period of 10 hours. The catalyst is removed and the liquid is concentrated, and after that the obtained solid is washed with ethyl alcohol, whereby 9.2 g of Compound 4 are obtained.

(Synthesis of Compound 5)

Nine point two grams (0.021 mole) of the above-obtained Compound 4 and 7.1 g (0.021 mole) of α-(2,4-di-t-pentylphenoxy)butyroyl chloride are dissolved into 100 ml of tetrahydrofuran, and to the solution are added 1.7 g (0.021 mole) of pyridine, and the reaction of the mixture takes place for two hours. The produced pyridine hydrochloride is filtered off, and the filtrate is concentrated to thereby produce a redish-brown viscous product, which is then subjected to a silica gel column treatment with use of a mixture solvent of chloroform with n-hexane in the proportion of 1:1, whereby 10 g of a light yellow thick syrup-like product as Compound 5.

(Synthesis of Exemplified Compound C-9)

Seven grams of the above-obtained Compound 5 are dissolved into 50 ml of ethyl alcohol, and to the solution is added a solution of 6.0 g of potassium hydroxide dissolved into 10 ml of water, and the reaction of the mixture takes place for three hours. The reaction product is then poured, with stirring, into an iced water containing 10 ml of concentrated hydrochloric acid, whereby white crystals are produced. The crystals are filtered, washed with water and then with acetonitrile, and further recrystallized from an acetonitrile-ethyl acetate mixture liquid, whereby 4.7 g of Exemplified Compound C-9 are obtained.

The structure of the above-obtained objective compound was confirmed by mass spectrometry.

As has been described, the silver halide photographic light-sensitive material of the present invention comprises a plurality of same spectral sensitivity-having silver halide emulsion layers, of which the highest-speed emulsion layer contains a nondiffusible coupler capable of producing the above-detailed movable dye and of which the lower-speed emulsion layer contains a DIR compound.

In the present invention, the DIR compound contained in the foregoing lower-speed emulsion layer is a compound capable of releasing a development inhibitor material by the reaction thereof with the oxidized product of a color developing agent.

As typical ones of such the DIR compound, there are those so-called DIR couplers into the active site of which is introduced a group capable of forming a compound having development inhibitability when split from the active site. Those DIR couplers of the kind are described in, e.g., British Patent No. 953,454, U.S. Pat. Nos. 3,227,554, 4,095,984, and 4,149,886.

The above-mentioned DIR couplers have the nature that the coupler's mother nucleus forms a dye during the coupling reaction thereof with the oxidized product of a color developing agent, and concurrently releases a development inhibitor material.

The present invention also include those compounds which, during the coupling reaction thereof with the oxidized product of a color developing agent, release a development inhibitor material but do not form any dye, as described in U.S. Pat. Nos. 3,652,345, 3,928,041, 3,958,993, 3,961,959 and 4,052,213, and Japanese Patent O.P.I. Publication Nos. 110529/1978, 13333/1979 and 161237/1980.

Further, the present invention includes the so-called timing DIR compounds wherein, during the reaction thereof with the oxidized product of a color developing agent, the mother nucleus forms a dye or a colorless compound, while the split-off timing group, by the intramolecular nucleophilic substitution reaction or split-off reaction, releases a development inhibitor material, as described in Japanese Patent O.P.I. Publication Nos. 145135/1979 and 114946/1981, and Japanese Patent Application No. 39766/1981.

Furthermore, the invention also includes those diffusible timing DIR compounds as described in Japanese Patent Application Nos. 44831/1982 and 45807/1982, wherein, during the reaction thereof with the oxidized product of a color developing agent, the diffusible dye-producible coupler's mother nucleus has the foregoing timing group linked thereto.

According to the present invention, those more preferred DIR compounds are represented by the following Formula (VII) or Formula (VIII):

COUP - inhibitor        Formula (VII)

wherein COUP represents a coupler component capable of coupling with the oxidized product of a color developing agent, the component including such dye-formable couplers as, e.g., open-chain ketomethylene compounds of acylacetanilides, pyrazolones, pyrazolotriazoles, pyrazolobenzimidazoles, indazolones, phenols, naphthols, and the like, and such coupling components substantially not forming any dye as acetophenones, indanones, oxazolones, and the like.

The inhibitor in the above formula is a compound that inhibits the development of silver halides, and those preferred compounds of the kind include such heterocyclic compounds and heterocyclic mercapto compounds as benzotriazole, 3-octylthio-1,2,4-triazole, and the like.

The above heterocyclic group includes tetrazolyl groups, thiadiazolyl groups, oxadiazolyl groups, thiazolyl groups, oxazolyl groups, imidazolyl groups, triazolyl groups, and the like; and to be more concrete, 1-phenyl-tetrazolyl group, 1-ethyl-tetrazolyl group, 1-(4-hydroxyphenyl)tetrazolyl group, 1,3,4-thiazolyl group, 5-methyl-1,3,4-oxadiazolyl group, benzothiazolyl group, benzoxazolyl group, benzimidazolyl group, 4H-1,2,4-triazolyl group, and the like.

COUP-TIME-inhibitor        Formula (VIII)

wherein inhibitor is as defined in Formula (VII); COUP, in addition to being as defined in Formula (VII), also includes a completely diffusible dye-producible coupler component; and TIME includes those having the following Formulas (IX), (X) and (XI), but is not limited thereto:

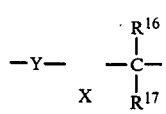

Formula (IX)

wherein X is a group of atoms necessary to complete a benzene or naphthalene ring; Y is

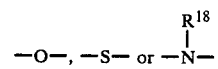

(wherein $R^{18}$ is a hydrogen atom, an alkyl group or an aryl group), any of which is linked to the ring in the coupling position thereof; and $R^{16}$ and $R^{17}$ each is as defined in $R^{18}$, but the group of

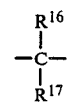

is substituted in the ortho or para position to the Y and bonded with the hetero atom contained in the inhibitor.

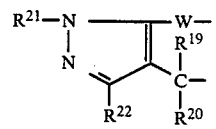

Formula (X)

wherein W is a group as defined in the Y of Formula (IX); $R^{19}$ and $R^{20}$ are as defined in the $R^{16}$ and $R^{17}$, respectively, of Formula (IX); $R^{21}$ is a hydrogen atom, an alkyl group, an aryl group, an acyl group, a sulfone group, an alkoxycarbonyl group or a heterocyclic residue; and $R^{22}$ is a hydrogen atom, an alkyl group, an aryl group, a heterocyclic residue, an alkoxy group, an amino group, an acylamido group, a sulfonamido group, carboxy group, an alkoxycarbonyl group, a carbamoyl group, or a cyano group. And the timing group is linked by W to COUP in the coupling position thereof and bonded by the

to the hetero atom of the inhibitor. The following is an exemplified Formula (XI) representing those timing groups releasing the inhibitor by the intramolecular nucleophilic substitution reaction:

Formula (XI)

wherein Nu is an electron-rich nucleophilic group having an oxygen, sulfur or nitrogen atom and is linked to COUP in the coupling position thereof; E is an electron-poor electrophilic group having a carbonyl, thiocarbonyl, phosphonyl or thiophosphinyl group and is bonded to the hetero atom of the inhibitor; and V is a linkage group which establishes the steric relation of Nu with E, and which, after Nu is released from COUP, is subjected to the intramolecular nucleophilic substitution reaction accompanied by the formation of 3- to 7-member cyclic ring, and is thereby capable of releasing an inhibitor.

The following are typical examples of the DIR compound of the present invention, but the present invention is not limited thereto.

Exemplified Compounds:

Exemplified Compounds:

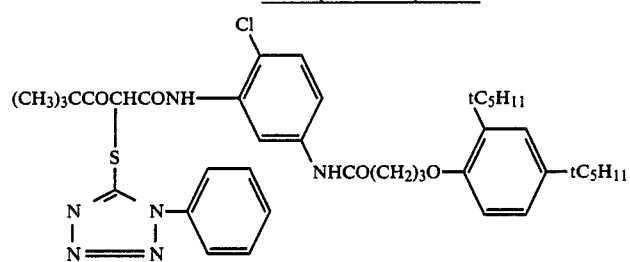

(D-1)

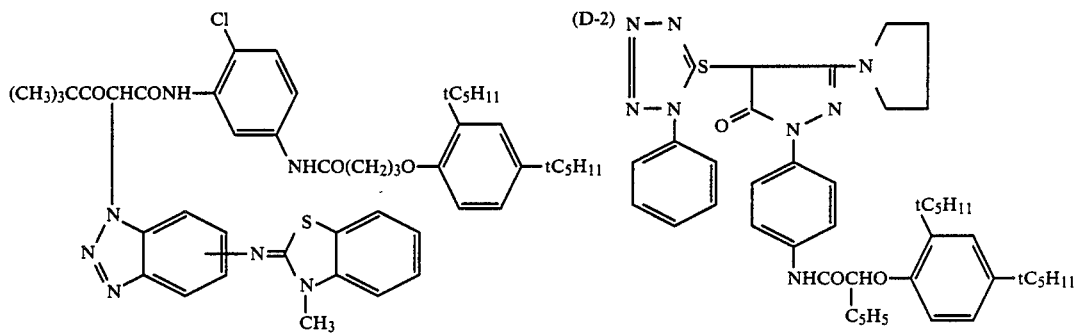

(D-2)

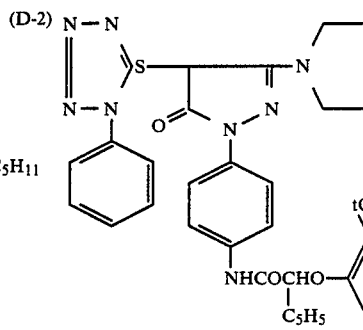

(D-3)

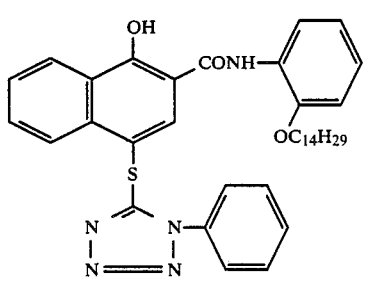

(D-4)

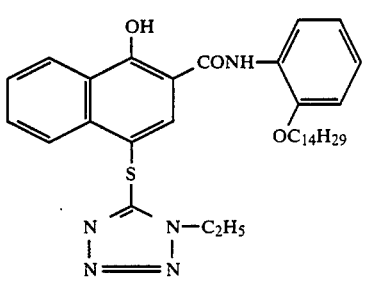

(D-5)

-continued
Exemplified Compounds:
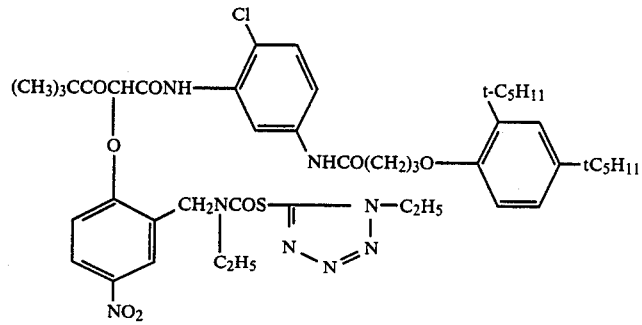
(D-6)
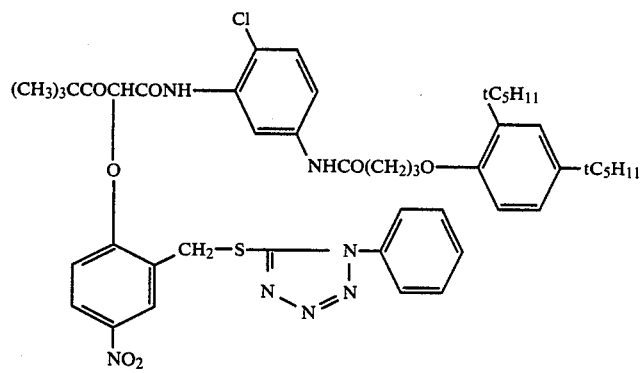
(D-7)
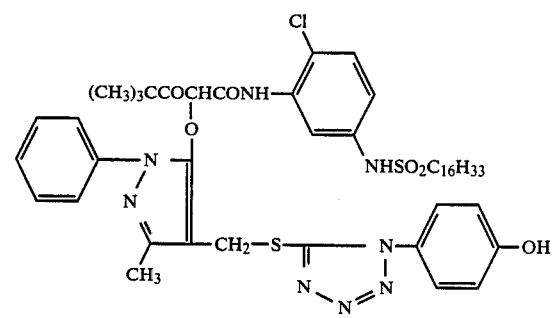
(D-8)
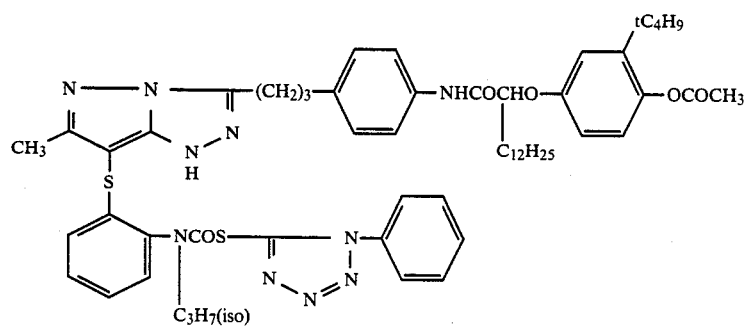
(D-9)

-continued
Exemplified Compounds:
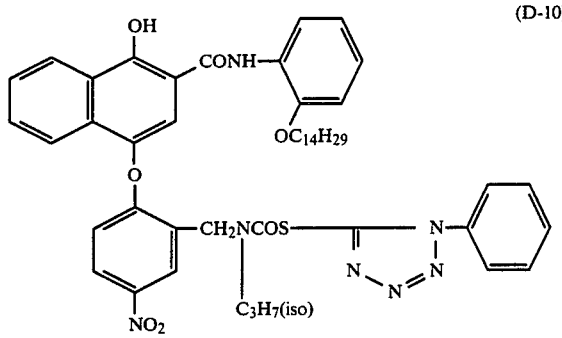 (D-10)
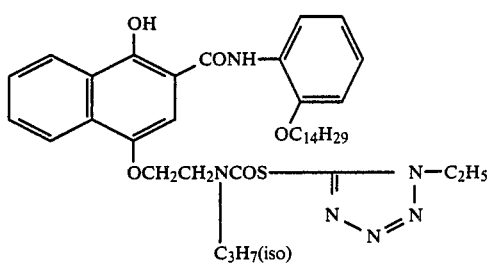 (D-11)
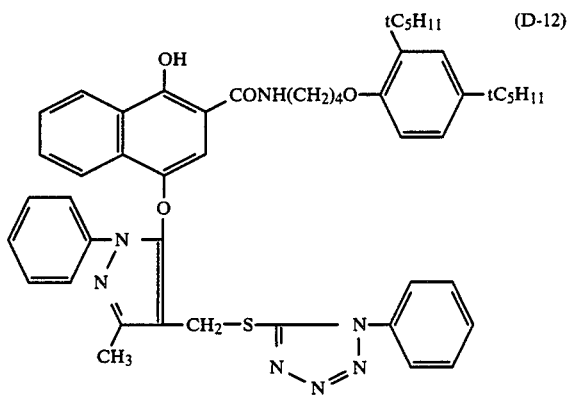 (D-12)
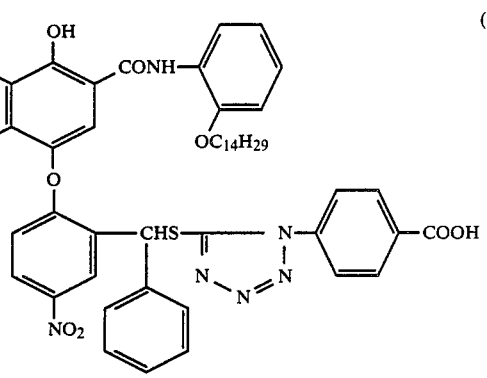 (D-13)
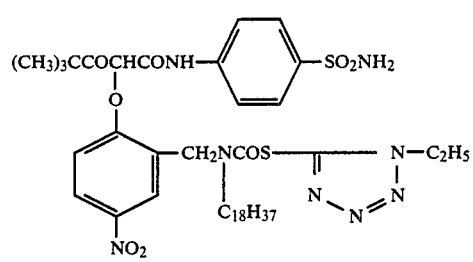 (D-14)
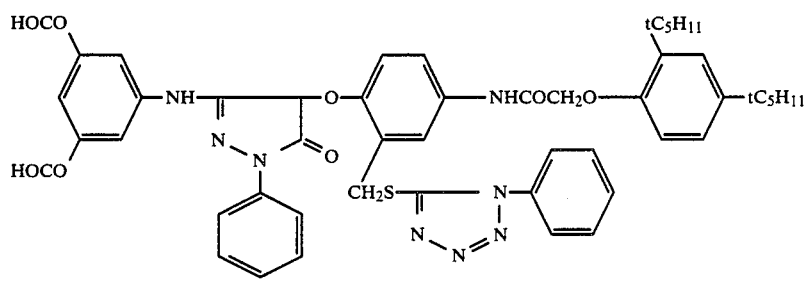 (D-15)

-continued
Exemplified Compounds:

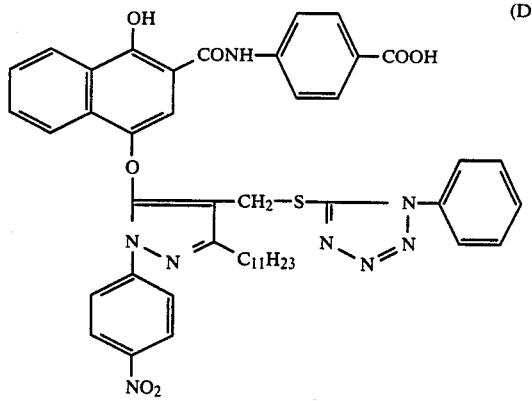
(D-16)

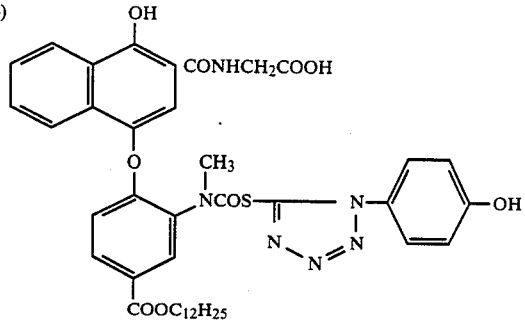
(D-17)

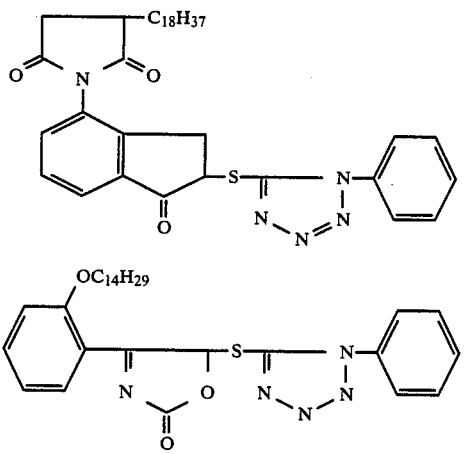
(D-18)

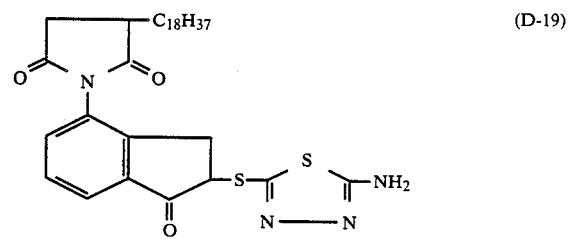
(D-19)

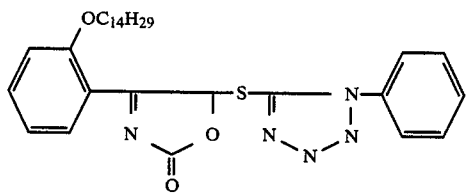
(D-20)

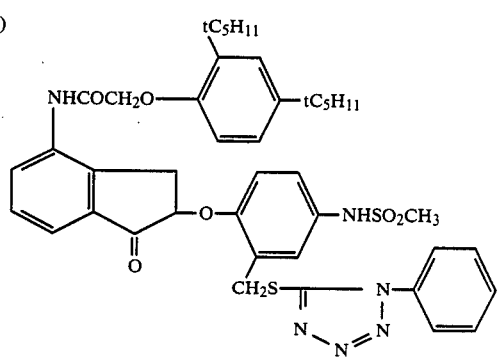
(D-21)

These DIR compounds can be synthesized in the manner as described in U.S. Pat. Nos. 3,227,554, 3,615,506, 3,632,345, 3,928,041, 3,933,500, 3,938,996, 3,958,993, 3,961,959, 4,046,574, 4,052,213, 4,063,950, 4,095,984 and 4,149,886, Japanese Patent O.P.I. Publication Nos. 81144/1975, 81145/1975, 13239/1976, 64927/1976, 104825/1976, 105819/1976, 65433/1977, 82423/1977, 117627/1977, 130327/1977, 154632/1977, 7232/1978, 9116/1978, 29717/1978, 70821/1978, 103472/1978, 110529/1978, 135333/1978, 143223/1978, 13333/1979, 49138/1979, 114241/1979, 145135/1979, 161237/1980 and 114946/1981, and Japanese Patent Application Nos. 39766/1981, 44831/1982 and 45807/1982, and the like.

The nondiffusible dye-producible nondiffusible coupler used for both high-speed emulsion layer and low-speed emulsion layer in the present invention may be any of known dye-producible couplers capable of producing appropriate color tone-having nondiffusible dyes. Such the coupler is incorporated at least into a lower-speed silver halide emulsion layer, but allowed to be present in the highest-speed silver halide emulsion layer containing a movable dye-producible nondiffusible coupler.

In the present invention, the quantity of the foregoing movable dye-producible nondiffusible coupler to be incorporated into the highest-speed silver halide emulsion layer is within the range of from $2 \times 10^{-3}$ moles to $2 \times 10^{-1}$ moles per mole of silver, while the quantity of the nondiffusible dye-producible nondiffusible coupler to be used together in the above highest-speed emulsion layer may be selectively used within the range of from about 1/50 to about 10 times that of the above movable dye-producible nondiffusible coupler.

The preferred quantity range of the DIR compound used for the silver halide emulsion layer whose speed is lower than that of the above highest-speed layer is generally from $10^{-3}$ to $10^{-1}$ mole per mole of silver.

In the present invention, the mordant used together with the completely diffusible dye-producible nondiffusible coupler may be any mordant capable of fixing the dye produced as a result of the coupling reaction. Those preferred mordants include such basic polymer mordants as described in U.S. Pat. No. 3,958,995, Japanese Patent O.P.I. Publication Nos. 74430/1979 and 22766/1980, such polymers of aminoguanidine derivatives of vinyl-methyl ketone as described in U.S. Pat. No. 2,882,156, and such basic polymer mordants as described in U.S. Pat. Nos. 3,625,394, 2,709,590 and 3,393,033, and the like. Other useful mordants are described in U.S. Pat. No. 3,559,095 and on pages 30 to 32 of Research Disclosure Dec. 1976. These mordants may be either added to a silver halide emulsion layer or formed as an independent layer.

A gelatin inert layer and a silver halide emulsion layer may be present between the above-mentioned completely diffusible dye-producible nondiffusible coupler layer and the mordant layer, but the larger the space between the coupler and mordant layers, the more becomes the sharpness of the resulting dye image deteriorated. In order to minimize such deterioration of the sharpness, the mordant may be mixed into the coupler-containing layer as described above. The using quantity of the foregoing mordant may be from 0.1 to 5 g/m$^2$, and preferably from 0.3 to 1.5 g/m$^2$.

For the silver halide photographic light-sensitive material of the present invention there may be used colored couplers as masking couplers. As a colored magenta coupler as the masking coupler, a compound produced by the substitution of an arylazo group at the active site of a colorless magenta coupler is generally used, which includes those compounds as described in, e.g., U.S. Pat. Nos. 2,801,171, 2,983,608, 3,005,712, and 3,684,514, British Patent No. 937,621, and Japanese Patent O.P.I. Publication Nos. 123625/1974 and 131448/1974, and the like.

Further, there may also be used colored magenta couplers of the type that by the reaction thereof with the oxidized product of a color developing agent the produced dye runs out into a processing bath, as described in U.S. Pat. No. 3,419,391.

As a colored cyan coupler as the masking coupler there may be used a compound produced by the substitution of an arylazo group at the active site of a colorless cyan coupler is used, which includes those compounds as described in, e.g., U.S. Pat. Nos. 2,521,908 and 3,034,892, British Patent No. 1,255,111, and Japanese Patent O.P.I. Publication No. 22028/1973.

Further, there may also be used those colored cyan couplers of the type that by the reaction thereof with the oxidized product of a color developing agent the formed dye runs out into a processing bath, as described in U.S. Pat. No. 3,476,563, and Japanese Patent O.P.I. Publication Nos. 10135/1975 and 123341/1975.

In order to improve the photographic characteristics, the photographic light-sensitive material may also contain a colorless dye-formable coupler, the so-called competing coupler.

The silver halide photographic emulsion for use in the present invention comprises a hydrophilic macromolecular material such as gelatin into which is dispersed in the colloidal particle form silver chloride, silver bromide, silver chlorobromide, silver chloroiodide, silver iodobromide, or silver chloroiodobromide, which may be prepared in various manners.

The above silver halide photographic emulsion can be sensitized by chemical sensitizers of the prior art, which include noble-metallic sensitizers, sulfur sensitizers, selenium sensitizers, and reduction sensitizers, which may be used singly or in combination. Further, the silver halide photographic emulsion of the present invention may, if necessary, be spectrally sensitized by use of sensitizing dyes of the prior art.

It may be desirable for displaying sufficiently the effect of the present invention to use in the light-sensitive silver halide emulsion layer or the hydrophilic colloidal layer adjacent thereto by incorporating in combination a reducing agent or oxidation inhibitor including, e.g., sulfites (sodium sulfite, potassium sulfite, etc.), hydrogensulfites (sodium hydrogensulfite, potassium hydrogensulfite, etc.), hydroxylamines (hydroxylamine, N-methyl-hydroxylamine, etc.), sulfinates (sodium phenyl-sulfinate, etc.), hydrazines (N,N'-dimethyl-hydrazine, etc.), reductones (ascorbic acid, etc.), aromatic hydrocarbons having at least one hydroxyl group (p-aminophenol, gallic acid, catechol, pyrogallol, resorcinol, 2,3-dihydroxynaphthalene, etc.), and the like. Further, in order to improve the light resistance of the magenta dye image formed from the magenta coupler used in the present invention, there may be incorporated into the emulsion layer or the adjacent layer thereto p-alkoxyphenols or phenolic compounds.

The construction of the silver halide color photographic light-sensitive material of the present invention may be on the basis of the subtractive color process. As a rule, the fundamental construction of the material is comprised principally of three layers: a blue-sensitive layer containing an yellow coupler for the formation of an yellow dye, a green-sensitive layer containing a magenta coupler for the formation of a magenta dye, and a red-sensitive layer containing a cyan coupler for the formation of a cyan dye. Further, at least one of these three layers or all the layers each is desirable to be composed of two or three superposed layers to thereby improve such photographic characteristics as the color-forming characteristic, color reproductions, graininess of the color-formed dyes, and the like.

In addition to these fundamental emulsion layers, there may be appropriately used a protective layer as the topmost layer, interlayers and filter layers between the emulsion layers, subbing layer as the bottom layer, and further an antihalation layer to thereby enable to improve the protection, prevention of color stain, graininess, color reproductions, layer adhesiveness of the light-sensitive material.

These emulsion layers and other layers are coated by any of known methods on an appropriate support material such as laminated paper, cellulose acetate, polystyrene, or the like.

In order to prevent possible deterioration of the speed or occurrence of fog during the manufacture, storage, or processing of the color light-sensitive material, to the silver halide emulsion may be added various compounds including such a heterocyclic compound as, e.g., 1-phenyl-5-mercaptotetrazole, 3-methyl-benzothiazole, 4-hydroxy-6-methyl-1,3,3a,7-tetrazaindene, etc., a mercapto compound, a metallic salt, and the like.

The emulsion may be subjected to a hardening treatment in accordance with a usual manner.

To the above silver halide emulsion may be added a single surfactant or a mixture of surfactants. As the surfactant, there may be used various active agents as coating aid, emulsifying agent, improving agent for the permeability of processing liquids into the emulsion, deforming agent, antistatic agent, anti-adhesion agent, or for improving the photographic characteristics or controlling the physical property of the emulsion.

In the silver halide photographic light-sensitive material of the present invention, in order to prevent possible occurrence of unnecessary fog or stain due to the air oxidation of an aromatic primary amine developing agent or to prevent possible diffusion of the oxidized product of the color developing agent into the adjacent layers during processing, it is advantageous to use in the silver halide emulsion layers or interlayers those alkyl-substituted hydroquinone compounds as disclosed in U.S. Pat. Nos. 2,728,659, 2,732,300 and 3,700,453, and Japanese Patent O.P.I. Publication No. 15438/1975 and Japanese Patent Application No. 2551/1979.

To incorporate into the silver halide photographic light-sensitive material the compounds to be contained in the highest-speed and lower-speed emulsion layers of the present invention, the compounds may be incorporated in various manners into the coating liquids of the component layers to contain the same, and to the incorporation may be applied various techniques that have conventionally been used for couplers; for example, the incorporation is made by dissolution into a high-boiling solvent as described in U.S. Pat. No. 2,322,027; a coupler and a high-boiling solvent are separately dispersed in the finely particulate form, and then mixed to be incorporated as described in U.S. Pat. No. 2,801,170; or in the dispersing method, the use of a low-boiling solvent may be advantageous. In this instance, the compounds of the present invention can be mixed with the coupler to be dispersed or can also be dispersed separately from the dispersion of the coupler and then used together. In the case of using a low-boiling solvent, it is possible to remove the low-boiling solvent from the dispersed liquid by such a method as described in U.S. Pat. No. 2,801,171 or in Japanese Patent Examined Publication No. 8099/1974.

Those particularly preferred among the applicable solvents to the invention include, as high-boiling solvents, dibutyl phthalate, dioctyl phthalate, diisodecyl phthalate, triphenyl phosphate, tricresyl phosphate, diethyl laurylamide, dibutyl laurylamide, benzyl phthalate, monophenyl-p-t-butylphenyl phosphate, phenoxyethanol, diethylene-glycol-monophenyl ether, dimethoxyethyl phthalate, hexamethylphosphoramide, and further those high-boiling organic solvents not miscible with water as described in U.S. Pat. No. 3,779,765, Japanese Patent O.P.I. Publication No. 90523/1974, and Japanese Patent Examined Publication No. 29060, and as low-boiling solvents, for example, methyl-isobutyl ketone, $\beta$-ethoxyethyl acetate, methoxytriglycol acetate, acetone, methyl acetone, methanol, ethanol, acetonitrile, dioxane, dimethylformamide, dimethylsulfoxide, ethyl acetate, butyl acetate, isopropyl acetate, butanol, chloroform, cyclohexane, cyclohexanol, fluorinated alcohol, and the like, and any of these low-boiling solvents may be used in place of or by mixing with any of the foregoing high-boiling solvents. Further, these solvents may be used singly or in combination of not less than two.

In addition, as another method, in the case of a water-soluble group-having coupler and of the compound of the present invention, the Fischer-type method, i.e., a method wherein they are dissolved into an alkaline liquid thereby to be used can be applied, or alternatively, a method wherein either one of the coupler and the compound of the invention may be incorporated by the dispersion method and the other by the Fischer-type method into the same layer.

A color developer for use in developing the silver halide photographic light-sensitive material of the present invention is an aqueous alkaline solution containing a color developing agent, whose pH is not less than 8, and preferably from 9 to 12. An aromatic primary amino developing agent as the developing agent means a compound or a precursor forming such the compound having a primary amino group and being capable of developing an exposed silver halide to light.

The above-mentioned developing agent is typified by p-phenylenediamine-type compounds, the preferred examples of which include 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 3-methyl-4-amino-N-ethyl-N-$\beta$-methanesulfonamidoethylaniline, 3-methyl-4-amino-N-ethyl-N-$\beta$-methoxyethylaniline, 3-$\beta$-methanesulfonamidoethyl-4-amino-N,N-diethylaniline, 3-methoxy-4-amino-N-ethyl-N-$\beta$-hydroxyethylaniline, 3-methoxy-4-amino-N-ethyl-$\beta$-methoxyethylaniline, 3-acetamido-4-amino-N,N-diethylaniline, 4-amino-N,N-dimethylaniline, N-ethyl-N-$\beta$-[$\beta$-($\beta$-methoxyethoxy)ethoxy]ethyl-3-methyl-4-aminoaniline, N-ethyl-N-$\beta$-($\beta$-methoxyethoxy)ethyl-3-methyl-4-aminoaniline, and salts of these compounds such as sulfates, hydrochlorides, sulfites, p-toluenesulfonates, and the like.

Further, there may be used those compounds as described in Japanese Patent O.P.I. Publication Nos. 64932/1973, 131526/975 and 95849/1976, and Pent et al. the Journal of American Society Vol. 73, pages 3100-3125 (1951), and the like. To these color developing agents may, if necessary, be added various additives such as alkali agent, pH control agent or buffer, development accelerator, antifoggant, preservative, and the like.

The color photographic light-sensitive material of the present invention, after exposed imagewise and subjected to a color development, can be processed in a bleaching bath in usual manner. This processing may be either performed concurrently with or separately from fixing. This bleaching bath, by adding, if necessary, a fixing agent thereto, can be used as a bleach-fix bath. As the bleaching agent, various compounds may be used together with a bleach accelerator and other additives.

The present invention will be illustrated further in detail with reference to examples below, but the invention is not limited thereto.

EXAMPLE 1

A multilayer color negative light-sensitive material was prepared as Sample 1, which has the following construction (layer weight: g/m$^2$) comprising a support having thereon dye image formable blue-sensitive, green-sensitive and red-sensitive silver halide emulsion layers.

| Layer 1 | mordant layer: | |
| --- | --- | --- |
| | gelatin | 1.80 |
| | mordant (the following Compound 1) | 1.00 |
| Layer 2 | gelatin layer | |
| Layer 3 | ultraviolet absorbing agent | |
| Layer 4 | high-speed blue-sensitive emulsion layer: | |
| | silver iodobromide (7 mole % silver iodide) | 1.20 |
| | gelatin | 1.75 |
| | exemplified coupler (C-3) | 0.31 |
| Layer 5 | low-speed blue-sensitive emulsion layer: | |
| | silver iodobromide (6 mole % silver iodide) | 1.55 |
| | gelatin | 2.14 |
| | yellow coupler (the following Compound 2) | 0.66 |
| | exemplified DIR compound (D-18) | 0.05 |
| Layer 6 | yellow filter layer | |
| Layer 7 | green-sensitive emulsion layer | |
| Layer 8 | red-sensitive emulsion layer | |
| Layer 9 | antihalation layer | |
| Support | cellulose triacetate film base | |

Sample 2 was subsequently prepared in quite the same manner as in Sample 1 with the exception that the exemplified DIR compound (D-18) was excluded and the silver halide was reduced in the quantity to 1.00 g/m².

On the other hand, Sample 3 also was prepared in quite the same manner as in Sample 1 with the exception that an yellow coupler (the following Compound 2) 0.34 g/m² was used in place of the exemplified coupler (C-3) of the high-speed blue-sensitive eumulsion layer, and teh mordant layer was excluded.

Sample 3' also was prepared in the same manner as in Sample 2 except that following yellow Compound 2 was used in place of Exemplified Coupler (C-3).

The above exemplified coupler (C-3) is a diffusible dye-producible coupler, which the coupler as the following Compound 2 and other couplers used in Samples 1 to 3' are all non-diffusible dye-producible couplers. The reason that the quantity of the silver halide was reduced in Sample 2 is because all the samples should be adjusted so as to indicate almost equal characteristic curves.

[Compound 1... mordant]

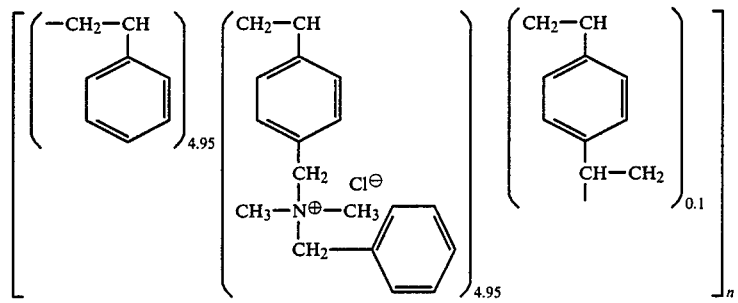

[Compound... yellow coupler]

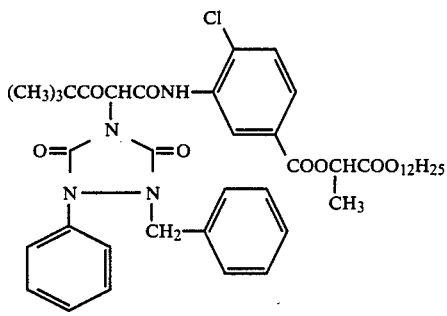

The thus obtained Samples 1 to 3' each was subjected to an wedge exposure in usual manner, and then processed in the following liquids in accordance with the development process steps below, thereby obtaining the results as given in Table 1. In addition, in regard to the red-sensitive and green-sensitive layers that showed substantially the same response in the present example, descriptions of their results are omitted herefrom.

| Development Process Steps: | |
|---|---|
| Steps (38° C.) | Processing Time |
| Color developing | 3 min. 15 sec. |
| Bleaching | 6 min. 30 sec. |
| Washing | 3 min. 15 sec. |
| Fixing | 6 min. 30 sec. |
| Washing | 3 min. 15 sec. |

| -continued | |
|---|---|
| Development Process Steps: | |
| Stabilizing | 1 min. 30 sec. |

Compositions of the respective processing liquids used in the development process are as follows:

| Color Developer Composition: | |
|---|---|
| 4-amino-3-methyl-N—ethyl-(β-hydroxyethyl)-aniline sulfate | 4.75 g |
| Anhydrous sodium sulfite | 4.25 g |
| Hydroxyamine ½ sulfate | 2.0 g |
| Potassium carbonate | 37.5 g |
| Sodium bromide | 1.3 g |
| Trisodium nitrilotriacetate, monohydrated | 2.5 g |
| Potassium hydroxide | 1.0 g |
| Water to make 1 liter | |
| Use potassium hydroxide to adjust the pH to 10.0 | |
| Bleaching Bath Composition: | |
| Iron-ammonium ethylenediamine tetraacetate | 100.0 g |
| Diammonium ethylenediamine tetraacetate | 10.0 g |
| Ammonium bromide | 150.0 g |
| Glacial acetic acid | 10 ml |
| Water to make 1 liter | |
| Use aqueous ammonia to adjust the pH to 6.0 | |
| Fixer Composition: | |
| Ammonium thiosulfate (aqueous 50% solution) | 162 ml |
| Anhydrous sodium sulfite | 12.4 g |
| Water to make 1 liter | |
| Use acetic acid to adjust the pH to 6.5 | |
| Stabilizer Composition: | |
| Formalin (aqueous 37% solution) | 5.0 ml |
| Koniducks (product of Konishiroku Photo Industry Co., Ltd.) | 7.5 ml |
| Water to make 1 liter | |

Each of the samples processed in the above processing baths was measured for the granularity of the developed dye image thereof in a blue light by the RMS(Root Mean Square) method using a microdensitometer having a 25-micron diameter circular scanning head. And the measured results are given in Table 1 in the normalized granularities (δN) obtained at densities 1.2 and 2.3.

The normalized granularity can be obtained by first subtracting from the density of the masking colored coupler in the film the contribution to the above density, and then by dividing the RMS granularity by the subtracted density.

On the other hand, each of Samples 1 to 3 was exposed so that its density becomes 1.8 to soft X-rays through a wedge having spatial frequencies varied in the range of from 3 lines/mm to 100 lines/mm, and processed in the same manner as previously described. The obtained color image was used to obtain MTF(Modulation Transfer Function) using a blue light. The resulting MTF values under the spatial frequency condition of 30 lines/mm are as given in Table 1. The MTF value is obtained by the density measurement made through a slitter with the dimensions of 300 microns by 2 microns, and shown in percentage of the output to the input.

In addition, the speed values given in Table 1 are each represented by the relative speed to the speed of Sample 1 regarded as 100.

TABLE 1

| Sample No. | Speed | γ2 | Lowest density | Highest density | δN × 1,000 D = 1.2 | δN × 1,000 D = 2.3 | MTF 30 lines/mm |
|---|---|---|---|---|---|---|---|
| 1 | 100 | 0.65 | 0.81 | 3.24 | 43 | 19 | 93 |
| 2 | 102 | 0.63 | 0.83 | 3.17 | 43 | 27 | 74 |
| 3 | 97 | 0.66 | 0.81 | 3.26 | 56 | 23 | 95 |
| 3' | 101 | 0.63 | 0.82 | 3.16 | 60 | 27 | 87 |

As apparent from Table 1, although Samples 1 to 3 all provide almost equal characteristic curve, Sample 1 for the present invention is excellent in the sharpness as well as in the granularity as compared to Samples 2 and 3.

EXAMPLE 2

A multilayer color negative light-sensitive material was prepared by coating on a transparent polyethylene terephthalate support the following layers in the described order from the support side, and this was regarded as Sample 4.

First layer . . . antihalation layer:

An aqueous gelatin solution containing black colloidal silver was coated so that the silver quantity is 0.3 g/m² and the dry thickness becomes 3.0μ.

Second layer . . . interlayer:

An aqueous gelatin solution was coated so that the dry thickness becomes 1.0μ.

Third layer . . . red-sensitive low-speed silver halide emulsion layer:

A silver iodobromide emulsion (a mixture of a silver iodobromide emulsion of mean particle size of 0.6μ containing 4 mole % of silver iodide with a silver iodobromide emulsion of mean particle size of 0.3μ containing 4 mole % of silver iodide in the proportion of 2:1) was chemically sensitized by the addition thereto of gold and sulfur sensitizers and further spectrally sensitized by the incorporation thereinto of redsensitizing dyes anhydrous 9-ethyl-3,3'-(3-sulfopropyl)-4,5,4',5'-dibenzothiacarbocyanine-hydroxide, anhydrous 5,5-dichloro-9-ethyl-3,3'-di-(3-sulfobutyl)thiacarbocyanine-hydroxide, and anhydrous 2-[2-{(5-chloro-3-ethyl-2(3H)-benzothiazolidene)methyl}-1-butyl-5-chloro-3-(4-sulfobutyl)benzoxazolium, and after that 1.0 g of 4-hydroxy-6-methyl-1,3,3a,7-tetrazaindene and 20.0 mg of 1-phenyl-5-mercaptotetrazole, thereby preparing a red-sensitive low-speed emulsion.

To this emulsion was added a dispersed mixture liquid prepared in the manner that per mole of silver halide 59 g of a cyan coupler 1-hydroxy-N-[δ-(2,4-di-t-aminophenoxy)butyl]2-naphthoamide, 4 g of a colored cyan coupler disodium 1-hydroxy-4-[4-(1-hydrox-8-acetamido-3,6-disulfo-2-naphthylazo)phenoxy]-N-[δ-(2,4-di-t-amylphenoxy)butyl]-2-naphthoamide, 6.2 g of Exemplified Compound D-12 as a DIR compound, and 0.5 g of dodecyl gallate were dissolved by heating into a mixture solvent of 65 g of dibutyl phthalate with 136 ml of ethyl acetate, and the resulting solution was added to 550 ml of an aqueous 7.5% gelain solution containing 5 g of sodium triisopropylnaphthalenesulfonate, and the resulting mixture was emulsified to be dispersed by a colloid mill, whereby a red-sensitive low-speed emulsion (containing 160 g of gelatin per mole of silver halide) was prepared, which was then coated so that the dry thickness becomes 40μ.

Fouth layer . . . red-sensitive high-speed silver halide emulsion layer:

A silver iodobromide emulsion (of mean particle size of 1.2μ, containing 7 mole % of silver iodide) was chemically sensitized by the addition thereto of gold and sulfur sensitizers, and further spectrally sensitized by the addition thereto of red-sensitizing dyes anhydrous 9-ethyl-3,3'-di-t-(3-sulfopropyl)-4,5,4'5'-dibenzothiacarbocyanine-hydroxide, anhydrous 5,5'-dichloro-9-ethyl-3,3'-di-(3-sulfobutyl)thiacarbocyaninehydroxide, and anhydrous 2-[2-{(5-chloro-3-ethyl-2(3H)-benzothiazolidene)methyl}-1-butenyl-5-chloro-3-(4-sulfobutyl)benzoxazolium, and after that 1.0 g of 4-hydroxy-6-methyl-1,3,3a,7-tetrazaindene and 10.0 ml of 1-phenyl-5-mercaptotetrazole were added, thereby preparing a red-sensitive high-speed emulsion.

To this emulsion was added a dispersed mixture liquid prepared in the manner that per mole of silver halide 28 g of a cyan coupler Exemplified Coupler C-22, 12 g of 1-hydroxy-4-isopropylaminocarbonylmethoxy-N-dodecyl-2-naphthoamide, 4 g of a colored cyan coupler disodium 1-hydroxy-4-[4-(1-hydroxy-8-acetamido-3,6-disulfo-2-naphthylazo)phenoxy]-N-[δ-(2,4-di-t-amylphenoxy)butyl]-2-naphthoamide, 0.5 g of dodecyl gallate, and 0.5 g of 2,5-di-t-octyl-hydroquinone were dissolved by heating into a mixture of 20 g of dibutyl phthalate with 60 ml of ethyl acetate, and this solution was added to 300 ml of an aqueous 7.5% gelatin solution containing 1.5 g of sodium triisopropyl-naphthalenesulfonate, and emulsified to be dispersed by means of a colloid mill, thereby preparing a red-sensitive high-speed emulsion (containing 160 g of gelatin per mole of silver halide), which was then coated so that the dry thickness becomes 2.0μ.

Fifth layer . . . interlayer:

The same as the second layer;

Sixth layer . . . green-sensitive low-speed silver halide emulsion layer:

A silver iodobromide emulsion of mean particle size of 0.6μ containing 4 mole % of silver iodide and a silver iodobromide emulsion of mean particle size of 0.3μ containing 7 mole % of silver iodide each was chemically sensitized by the addition thereto of gold and sulfur sensitizers, and further spectrally sensitized by the addition thereto of green-sensitizing dyes anhydrous 5,5'-dichloro-9-ethyl-3,3'-di-(3-sulfobutyl)oxacarbocyanine-hydroxide, anhydrous 5,5'-diphenyl-9-ethyl-3,3-di-(3-sulfobutyl)oxacarbocyanine-hydroxide, and anhydrous 9-ethyl-3,3-di-(3-sulfopropyl)-5,6,5',6'-dibenzoxacarbocyanine-hydroxide, and then 1.0 g of 4-hydroxy-6-methyl-1,3,3a,7-tetrazaindene and 20.0 ml of 1-phenyl-5-mercaptotetrazole were added to thereby produce separately in usual manner two emulsions. The thus produced two emulsions were mixed in the proportion of 1:1, whereby a green-sensitive low-speed silver halide emulsion was prepared.

Further, to the resulting emulsion was added a dispersed mixture liquid prepared in the manner that per mole of silver halide 80 g of a magenta coupler 1-(2,4,6-trichlorophenyl)-3-{3-(4-dodecyloxyphenyl)sulfonamidobenzamido}-pyrazoline-5-one, 35 g of Exemplified Coupler C-18, 5.3 g of Exemplified DIR Compound D-16 as a DIR compound, 2.5 g of a colored magenta coupler 1-(2,4,6-trichlorophenyl)-4-(1-naphthylazo)-3-(2-chloro5-octadecenylsuccinimidoanilino)-5-pyrazolone, and 0.5 g of dodecyl gallate were dissolved by heating into a mixture of 120 g of tricresyl phosphate and 240 ml of ethyl acetate, and the resulting solution was added to an aqueous gelatin solution containing triisopropyl-naphthalenesulfonate, and emulsified to be dispersed by means of a colloid mill, whereby a green-sensitive low-speed emulsion (containing 160 g of gelatin per mole of silver) was prepared, which was then coated so that the dry thickness becomes 4.0μ.

Seventh layer . . . green-sensitive high-speed silver halide emulsion layer:

A silver iodobromide emulsion (of mean particle size of 1.2μ, containing 7 mole % of silver iodide) was chemically sensitized by gold and sulfur sensitizers, and spectrally sensitized by the addition thereto of anhydrous 5,5'-dichloro-9-ethyl-3,3'-di-(3-sulfobutyl)oxacarbocyanine-hydroxide, anhydrous 5,5-diphenyl-9-ethyl-3,3'-di-(3-sulfobutyl)oxacarbocyanine-hydroxide and anhydrous 9-ethyl-3,3'-di-(3-sulfopropyl)5,6,5',6'-dibenzoxacarbocyanine-hydroxide, and further, 1,0 g of 4-hydroxy-6-methyl-1,3,3a,7-tetrazaindene and 10.0 mg of 1-phenyl-5-mercaptotetrazole were added, thereby preparing a green-sensitive high-speed silver halide emulsion.

Further, to the emulsion was added a dispersed mixture liquid prepared in the manner that 52 g of Exemplified Coupler C-18 as a magenta coupler, 30 g of 1-(2,4,6-trichlorophenyl)-3-{3-(2,4-di-t-amylphenoxyacetamido)benzamido}pyrazoline-5-one, 2.5 g of a colored magenta coupler 1-(2,4,6-trichlorophenyl)-4-(1-naphthylazo)-3-(2-chloro-5-octadecenylsuccinimidoanilino)-5-pyrazolone, and 15 g of 2,5-di-t-octyl-hydroquinone were dissolved by heating into a mixture of 120 g of tricresyl phosphate and 240 ml of ethyl acetate, and the solution was added to an aqueous gelatin solution containing sodium triisopropylnaphthalenesulfonate, and emulsified to be dispersed by means of a colloid mill, whereby a green-sensitive high-speed emulsion (containing 160 g of gelatin per mole of silver halide) was prepared, which was coated so that the dry thickness becomes 2.0μ.

Eighth layer . . . interlayer:
The same as the second layer.
Ninth layer . . . yellow filter layer:

To an yellow colloidal silver-dispersed aqueous gelatin solution was added a dispersed liquid that was prepared in the manner that 3 g of 2,5-di-t-octyl-hydroquinone and 1.5 g of di-2-ethyl-hexyl phthalate were dissolved into 10 ml of ethyl acetate, and this solution was dispersed into an aqueous gelatin solution containing 0.3 g of sodium triisopropyl-naphthalenesulfonate. The resulting mixture liquid was coated so that the coating quantity of the gelatin is 0.9 g/m$^2$, that of the 2,5-di-t-octyl-hydroquinon is 0.10 g/m$^2$, and the dry thickness becomes 1.2μ.

Tenth layer . . . blue-sensitive low-speed silver halide emulsion layer:

A silver iodobromide emulsion (of mean particle size of 0.6μ, containing 6 mole % of silver iodide) was chemically sensitized by gold and sulfur sensitizers and spectrally sensitized by the addition thereto of a blue-sensitizing dye anhydrous 5,5'-dimethoxy-3,3'-di-(3-sulfopropyl)thiacyanine-hydroxide, and then 1.0 g of 4-hydroxy-6-methyl-1,3,3a,7-tetrazaindene and 20.0 mg of 1-phenyl-5-mercaptotetrazole were added to thereby prepare in usual manner a blue-sensitive low-speed silver halide emulsion.

Further, to the emulsion was added a dispersed mixture liquid that was prepared in the manner that per mole of silver halide as yellow couplers 120 g of α-pivaloyl-α-(1-benzyl2-phenyl-3,5-dioxo-1,2,4-triazolidine-4-yl)-2-chloro-5-[α-(dodecyloxycarbonyl)ethoxycarbonyl]acetanilide acetanilide and 50 g of α-{3-[α-(2,4-di-t-amylphenoxy)butylamido}benzoyl-2-methoxyacetanilide, and 15 g of Exemplified Compound C-6 as a DIR compound were dissolved by heating into a mixture of 120 g of dibutyl phthalate and 300 ml of ethyl acetate, and this solution was added to an aqueous gelatin solution containing sodium triisopropyl-naphthalenesulfonate and emulsified to be dispersed by means of a colloid mill, whereby a blue-sensitive low-speed silver halide emulsion (containing 160 g of gelatin per mole of silver halide) was prepared, which was then coated so that the dry thickness becomes 4.0μ.

Eleventh layer . . . blue-sensitive high-speed silver halide emulsion layer:

A silver iodobromide emulsion (of mean particle size of 1.2μ, containing 7 mole % of silver iodide) was chemically sensitized by gold and sulfur sensitizers and spectrally sensitized by the addition thereto of a blue-sensitizing dye anhydrous 5,5'-dimethoxy-3,3'-di-(3-sulfopropyl)thiacyanine-hydroxide, and then 1.0 g of 4-hydroxy-6-methyl-1,3,3a,7-tetrazaindene and 10.0 mg of 1-phenyl-5-mercaptotetrazole were added to thereby prepare in usual manner a blue-sensitive high-speed silver halide emulsion.

Further, to the resulting emulsion was added a dispersed mixture liquid that was prepared in the manner that per mole of silver halide 80 g of Exemplified Coupler C-14 as an yellow coupler were dissolved by heating into a mixture of 80 g of dibutyl phthalate with 240 ml of ethyl acetate, and this solution was added to an aqueous gelatin solution containing sodium triisopropyl-naphthalenesulfonate, and emulsified to be dispersed by means of a colloid mill, whereby a blue-sensitive high-speed silver halide emulsion (containing 240 g of gelatin per mole of silver halide) was prepared, which was then coated so that the dry thickness becomes 2.0μ.

Twelfth layer . . . interlayer:

Two grams of di-2-ethyl-hexyl phthalate, 2 g of 2-[3-cyano-3-(n-dodecylaminocarbonyl)arylidene]-1-ethyl-pyrolidine and 2 ml of ethyl acetate were mixed, and the mixture was dispersed into an aqueous gelatin solution containing 0.6 g of sodium triisopropyl-naphthalenesulfonate, and this was coated so that the coating quantity of the gelatin is 1.0 g/m², and the dry thickness becomes 1.0μ.

Thirteenth layer . . . protective layer:

An aqueous gelatin solution containing per 100 ml 4 g of gelatin and 0.2 g of 1,2-bisvinyl-sulfonyl-ethane was coated so that the coating quantity of the gelatin is 1.3 g/m² and the dry thickness becomes 1.2μ.

On the other hand, Sample 5 as a comparative sample was prepared in the same manner as in Sample 4 with the exception that the DIR compound was excluded from Layers 3, 6 and 10 of Sample 4, and concurrently, in order to control so that almost the same characteristic curve as in Sample 4 can be obtained, the quantity of the silver halide of Layer 3 was reduced by 33%, that of Layer 6 by 50%, and that of Layer 10 by 35%.

The thus obtained samples each was slit into 35 mm size film to be photographed and processed, thereby obtaining negative film images, from which were made enlarged color photographic prints. The color prints were examined by comparison, and as a result, the color prints obtained from Sample 4 of the present invention showed very fine and sharp details from the shadow to the highlight with bright and clear color reproductions, which were particularly excellent in the green and red color reproductions.

In contrast to this, the color prints obtained from the comparative Sample 5 showed that not only is the coarse-grained tone conspicuous on the whole but the image lacks sharpness and, besides, is inferior in the color reproductions.

Thus, it is obvious that the present invention provides not only improvements on the graininess and sharpness but also a very excellent effect for color reproductions.

What is claimed is:

1. A silver halide photographic light-sensitive material comprising a support having thereon a plurality of silver halide emulsion layers which have different speeds but have sensitivites in the same spectral region, wherein at least one lower speed light-sensitive emulsion layer comprises a non-diffusible coupler capable of forming non-diffusible dye by reaction with an oxidation product of a color developing agent and a non-diffusible compound of releasing a development inhibitor by reaction with an oxidation product of a color developing agent, and the silver halide emulsion layer having the highest speed amongst said plurality of silver halide emulsion layers contains a non-diffusible coupler capable of producing a diffusible dye by reaction with an oxidation product of a color developing agent, wherein all silver halide emulsion layers sensitive to the same spectral region are adjacently positioned.

2. The silver halide photographic light-sensitive material of claim 1, wherein said light-sensitive layers whose light-sensitivities are substantially the same are one of a blue-sensitive layer, a green-sensitive layer and a red-sensitive layer.

3. The silver halide photographic light-sensitive material of claim 2, wherein a red-sensitive layer, a green-sensitive layer and a blue-sensitive layer are respectively coated in this order from the support side.

4. The silver halide photographic light-sensitive material of claim 2, wherein one of the red-sensitive layer, the green-sensitive layer and the blue-sensitive layer is formed of plural silver halide emulsion layers of which speeds are different from each other.

5. The silver halide photographic light-sensitive material of claim 2, wherein everyone of the red-sensitive layer, the green-sensitive layer and the blue-sensitive layer is formed of at least two silver halide emulsion layers of which speeds are different from each other.

6. The silver halide photographic light-sensitive material of claim 2, wherein, out of said plural silver halide emulsion layers of which speeds are different from each other, a layer adjacent to the support side is coated as a low speed layer.

7. The silver halide photographic light-sensitive material of claim 3, wherein the blue-sensitive layer is formed of at least two silver halide emulsion layers of which speeds are different from each other.

8. The silver halide photographic light-sensitive material of claim 1, wherein the movable dye-producible nondiffusion coupler is to produce a dye which is so slightly movable as desired within a period of time during which a processing and a drying are completed.

9. The silver halide photographic light-sensitive material of claim 1, wherein the movable dye-producible nondiffusion coupler is to produce a completely diffusible dye.

10. The silver halide photographic light-sensitive material of claim 1, wherein the movable dye-producible nondiffusion coupler has the Formula (I) below:

wherein COUP represents a coupler moiety for producing a dye, and the stabilizing group is a group that is linked to the above coupler moiety in the coupling position thereof and can be split from COUP during the coupling reaction between the coupler and the oxidized product of a color developing agent, and the above stabilizing group has such molecular size and form as enough for rendering the coupler nondiffusible, and the control group is a group that is linked to COUP in the noncoupling position thereof and so controls the dye produced by the coupling reaction of the coupler with the oxidized product of a color developing agent as to become slightly movable as previously described or completely diffusible.

11. The silver halide photographic light-sensitive material of claim 10, wherein the stabilizing group in Formula (I) is a group having an alkyl component and an aryl component having not less than eight carbon atoms.

12. The silver halide photographic light-sensitive material of claim 10, wherein the stabilizing group in Formula (I) is a group having an alkyl component and an aryl component having from 8 to 32 carbon atoms.

13. The silver halide photographic light-sensitive material of claim 10, wherein the stabilizing group in Formula (I) is an alkoxy group, an aryloxy group, an alkylthio group, an arylthio group or a nitrogen-containing hetero-cyclic group each having from 8 to 32 carbon atoms.

14. The silver halide photographic light-sensitive material of claim 10, wherein the control group in Formula (I) is an alkyl group having from 1 to 20 carbon atoms and an aryl group having from 6 to 20 carbon atoms.

15. The silver halide photographic light-sensitive material of claim 10, wherein the control group in Formula (I) is an alkali-soluble group capable of being ionized under a processing condition.

16. The silver halide photographic light-sensitive material of claim 10, wherein the nondiffusible coupler capable of producing the movable dye having Formula (I) has the Formula (II) below:

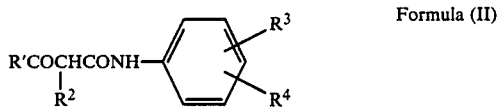

Formula (II)

wherein $R^1$ is an aryl group or an alkyl group; $R^2$ is the stabilizing group that is synonymous with that in Formula (I); $R^3$ is the control group that is synonymous with that in Formula (I); and $R^4$ is a hydrogen atom, a halogen atom, an alkyl group or an alkoxy group each having 1 to 8 carbon atoms, and a control group.

17. The silver halide photographic light-sensitive material of claim 10, wherein the nondiffusible coupler capable of producing the movable dye having Formula (I) has the Formulas (III) and (IV) below:

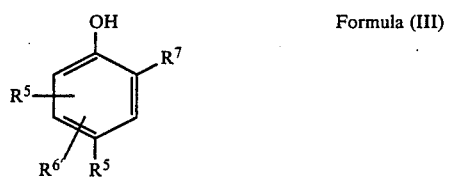

Formula (III)

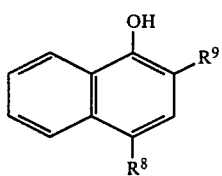

Formula (IV)

wherein $R^5$ represents a group the same as defined in the $R^2$ of Formula (II); any one of $R^6$, $R^{6'}$ or $R^7$ represents the foregoing control group and the other two of them are allowed to be either the same of different from each other, representing a hydrogen atom, a halogen atom, an alkyl group, an alkoxy group, an alkylamino group, or an acylamido group each having 1 to 8 carbon atoms; $R^8$ is a group the same as defined in $R^5$; and $R^9$ represents a control group.

18. The silver halide photographic light-sensitive material of claim 10, wherein the nondiffusible coupler capable of producing the movable dye having the Formula (I) has the Formulas (V) and (VI) below:

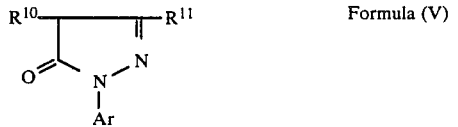

Formula (V)

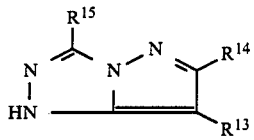

Formula (VI)

-continued wherein $R^{10}$ represents a group the same as defined in the $R^5$ of Formula (II); $R^{11}$ represents a control group; Ar is a phenyl group; $R^{13}$ is a group as defined in $R^{10}$; and either one of $R^{14}$ and $R^{15}$ is a control group and the other is a hydrogen atom, an alkyl group having 1 to 8 carbon atoms, an alkoxy group having 1 to 8 carbon atoms, an aryl group having 6 to 10 carbon atoms, an amono or acylamino group.

19. The silver halide photographic light-sensitive material of claim 1, wherein the nondiffusible compound capable of releasing a development inhibitor has the Formulas (VII) and (VIII) below:

COUP - inhibitor     Formula (VII)

wherein COUP represents a coupler component capable of coupling with the oxidized product of a color developing agent to produce a dye, or incapable of substantially producing any dye; and inhibitor is a compound that inhibits the development of silver halides:

COUP - TIME - inhibitor     Formula (VIII)

wherein inhibitor is the group synonymous with that in Formula (VII); COUP represents the group synonymous with that in Formula (VII) and a coupler component capable of producing a completely diffusible dye; and TIME represents the group having the Formulas (IX), (X) and (XI) below:

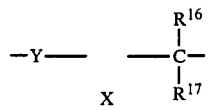

Formula (IX)

wherein X is a group of atoms necessary to complete a benzene or naphthalene ring; Y is

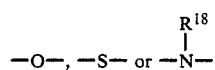

wherein $R^{18}$ is a hydrogen atom, an alkyl group or an aryl group, any of which is linked to the ring in the coupling position thereof; and $R^{16}$ and $R^{17}$ each is as defined in the $R^{18}$, but the group of

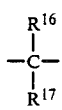

is substituted in the ortho or para position to the Y and bonded with the hetero atom contained in the inhibitor:

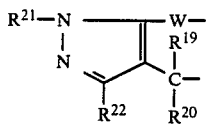

Formula (X)

wherein W is a group as defined in the Y of Formula (IX); $R^{19}$ and $R^{20}$ are as defined in the $R^{16}$ and $R^{17}$, respectively, of Formula (IX); $R^{21}$ is a hydrogen atom, an alkyl group, an aryl group, an acyl group, a sulfone group, an alkoxycarbonyl group or a heterocyclic residue; and $R^{22}$ is a hydrogen atom, an alkyl group, an aryl group, a heterocyclic residue, an alkoxy group, an amino group, an acylamido group, a sulfonamido group, carboxy group, an alkoxycarbonyl group, a carbamoyl group, or a cyano group, and the timing group is linked by W to COUP in the coupling position thereof and bonded by the

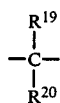

to the hetero atom of the inhibitor:

Formula (XI)

wherein Nu is an electron-rich nucleophilic group having an oxygen, sulfur or nitrogen atom and is linked to COUP in the coupling position thereof; E is an electron-poor electrophilic group having a carbonyl, thiocarbonyl, phosphonyl or thiophosphinyl group and is bonded to the hetero atom of the inhibitor; and V is a linkage group which establishes the steric relation of Nu with E, and which, after Nu is released from COUP, is subjected to the intramolecular nucleophilic substitution reaction accompanied by the formation of 3- to 7-member cyclic ring, and is thereby capable of releasing an inhibitor.

20. The silver halide photographic light-sensitive material of claim 19, wherein the inhibitor is benzotriazole, 3-octylthio-1,2,4,-triazole.

21. The silver halide photographic light-sensitive material of claim 1, wherein the movable dye-producible nondiffusible coupler to be incorporated into the highest-speed silver halide emulsion layer is within the range of from $2 \times 10^{-3}$ moles to $2 \times 10^{-1}$ moles per mole of silver.

22. The silver halide photographic light-sensitive material of claim 1, wherein the quantity range of the nondiffusible compound capable of releasing a development inhibitor is $10^{-3}$ to $10^{-1}$ mole per mole of silver so as to be added to the silver halide emulsion layer whose speed is lower than that of the highest speed layer.

23. The silver halide photographic light-sensitive material of claim 1, wherein the silver halide emulsion layer of the highest speed contains a mordant together with the nondiffusible coupler capable of producing a movable dye.

24. The silver halide photographic light-sensitive material of claim 23, wherein the amount of the mordant used is 0.1 to 5 $g/m^2$.

25. The silver halide photographic light-sensitive material of claim 24, wherein the amount of the mordant used is 0.3 to 1.5 $g/m^2$.

26. The silver halide photographic light-sensitive material of claim 1, wherein the support thereof bears thereon at least one or plural light-sensitive layers whose color-sensitivities are substantially the same and a mordant layer.

27. The silver halide photographic light-sensitive material of claim 1, wherein the highest-speed silver halide emulsion layer contains a movable dye-producible nondiffusible coupler and nondiffusible dye-producible nondiffusible coupler, and a silver halide emulsion layer having a lower speed than that of the above layer contains a nondiffusible dye-producible nondiffusible coupler and a DIR compound.

28. The silver halide photographic light-sensitive material of claim 1, wherein the highest-speed silver halide emulsion layer contains a movable dye-producible nondiffusible coupler and nondiffusible dye-producible nondiffusible coupler, and a silver halide emulsion layer having a lower speed than that of the above layer contains a movable dye-producible nondiffusible coupler, nondiffusible dye-producible nondiffusible coupler, and a DIR compound.

* * * * *

Adverse Decision in Interference

In Interference No. 102,392, involving Patent No. 4,774,053, S. Nakagwa, S. Kida, Y. Kawashima, K. Masuda, SILVER HALIDE PHOTOGRAPHIC LIGHT-SENSITIVE MATERIAL, final judgment adverse to the patentees was rendered June 18, 1990, as to claims 1-28.
*[Official Gazette August 28, 1990]*